(12) United States Patent
Ran et al.

(10) Patent No.: US 8,743,367 B2
(45) Date of Patent: Jun. 3, 2014

(54) OPTICAL RESONANCE ANALYSIS USING A MULTI-ANGLE SOURCE OF ILLUMINATION

(75) Inventors: Boaz Ran, Haifa (IL); Tal Rosenzweig, Kfar-Vradim (IL); Ariel G. Notcovich, Haifa (IL); Ariel Shemesh, Haifa (IL); Yochanan Uri, Givat Elah (IL); Michael Kanevsky, Tirat HaCarmel (IL); James W. Hillendahl, Vacaville, CA (US); Barak Abraham Liraz, Haifa (IL)

(73) Assignee: Bio-Rad Laboratories Inc., Hercules, CA (US)

( * ) Notice: Subject to any disclaimer, the term of this patent is extended or adjusted under 35 U.S.C. 154(b) by 549 days.

(21) Appl. No.: 12/451,547

(22) PCT Filed: May 21, 2008

(86) PCT No.: PCT/IL2008/000692
§ 371 (c)(1),
(2), (4) Date: Nov. 18, 2009

(87) PCT Pub. No.: WO2008/142689
PCT Pub. Date: Nov. 27, 2008

(65) Prior Publication Data
US 2010/0220330 A1    Sep. 2, 2010

Related U.S. Application Data

(60) Provisional application No. 60/924,554, filed on May 21, 2007.

(51) Int. Cl.
*G01N 21/55* (2014.01)
*G01J 4/00* (2006.01)

(52) U.S. Cl.
USPC .......................... 356/445; 356/364

(58) Field of Classification Search
None
See application file for complete search history.

(56) References Cited

U.S. PATENT DOCUMENTS

| | | | | | |
|---|---|---|---|---|---|
| 4,889,427 | A | * | 12/1989 | Van Veen et al. | 356/445 |
| 5,374,563 | A | * | 12/1994 | Maule | 436/165 |
| 5,479,260 | A | | 12/1995 | Fattinger | |
| 5,875,032 | A | * | 2/1999 | Naya | 356/445 |
| 5,917,607 | A | * | 6/1999 | Naya | 356/445 |
| 6,242,209 | B1 | * | 6/2001 | Ransom et al. | 435/29 |
| 6,417,924 | B1 | * | 7/2002 | Kimura | 356/445 |
| 6,507,402 | B2 | | 1/2003 | Negami et al. | |
| 6,570,657 | B1 | | 5/2003 | Hoppe et al. | |
| 6,734,956 | B2 | | 5/2004 | Byrne | |

(Continued)

FOREIGN PATENT DOCUMENTS

WO    WO 2008/142689    11/2008

OTHER PUBLICATIONS

International Preliminary Report on Patentability Dated Dec. 3, 2009 From the International Bureau of WIPO Re.: Application No. PCT/IL2008/000692.

(Continued)

*Primary Examiner* — Gordon J Stock, Jr.

(57) ABSTRACT

An SPR or other optical resonance based analysis system in which, light is provided at multiple angles to a specimen and then the light modified by the specimen is processed to select only some of the light. Optionally, the processing selects light at a particular incidence angle. Optionally, the detection is by imaging of the light on a 2D imager array.

27 Claims, 16 Drawing Sheets

(56) References Cited

U.S. PATENT DOCUMENTS

| | | |
|---|---|---|
| 6,873,417 B2 | 3/2005 | Bahatt et al. |
| 7,012,693 B2 | 3/2006 | Mori et al. |
| 7,057,720 B2 | 6/2006 | Caracci et al. |
| 7,057,731 B2 | 6/2006 | Naya |
| 7,196,787 B2 | 3/2007 | Uhl et al. |
| 7,217,542 B2 * | 5/2007 | Tyvoll et al. ................ 435/91.1 |
| 7,227,116 B2 * | 6/2007 | Gleckler .................... 250/208.1 |
| 2002/0001085 A1 | 1/2002 | Dickopf et al. |
| 2003/0076501 A1 | 4/2003 | Hofmann |
| 2003/0103208 A1 | 6/2003 | Quinn et al. |
| 2003/0124599 A1 * | 7/2003 | Chen et al. ........................ 435/6 |
| 2003/0179379 A1 | 9/2003 | Gedig |
| 2004/0263841 A1 | 12/2004 | Caracci et al. |
| 2005/0046853 A1 | 3/2005 | Sato |
| 2005/0099622 A1 * | 5/2005 | Caracci et al. ................ 356/300 |
| 2005/0134860 A1 * | 6/2005 | Chinowsky .................. 356/445 |
| 2005/0236554 A1 * | 10/2005 | Fontaine et al. ........... 250/208.1 |
| 2006/0017931 A1 * | 1/2006 | Kimura ........................ 356/445 |
| 2006/0072113 A1 | 4/2006 | Ran et al. |
| 2006/0092434 A1 * | 5/2006 | Koakutsu ...................... 358/1.1 |
| 2006/0119859 A1 | 6/2006 | Su et al. |
| 2006/0164633 A1 | 7/2006 | Koshoubu et al. |
| 2006/0182660 A1 | 8/2006 | Takayama et al. |
| 2006/0262313 A1 | 11/2006 | Bahatt et al. |
| 2007/0054415 A1 * | 3/2007 | Muraishi ...................... 436/518 |
| 2007/0109542 A1 * | 5/2007 | Tracy et al. .................. 356/445 |
| 2008/0163688 A1 * | 7/2008 | Wang et al. ..................... 73/580 |
| 2012/0113428 A1 * | 5/2012 | Ran et al. ...................... 356/445 |

OTHER PUBLICATIONS

International Search Report Dated Oct. 21, 2008 From the International Searching Authority Re.: Application No. PCT/IL2008/000692.

Written Opinion Dated Oct. 21, 2008 From the International Searching Authority Re.: Application No. PCT/IL2008/000692.

* cited by examiner

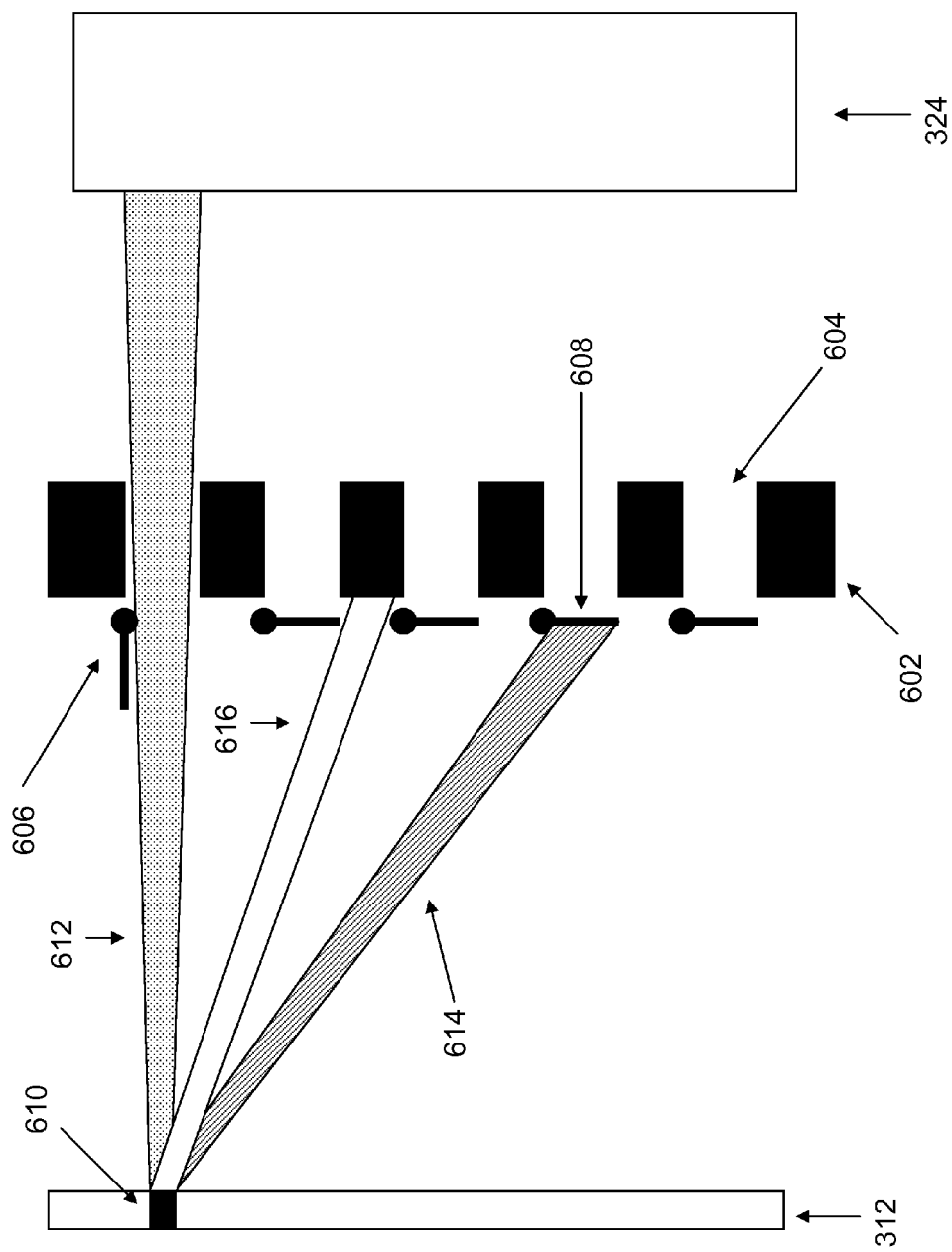

OPTICAL RESONANCE ANALYSIS USING A MULTI-ANGLE SOURCE OF ILLUMINATION

RELATED APPLICATION

This Application is a National Phase Application of PCT Patent Application No. PCT/IL2008/000692 having International Filing Date of May 21, 2008, which claims the benefit under 35 U.S.C. §119(e) of U.S. Provisional Application No. 60/924,554, filed on May 21, 2007. The contents of the above Applications are all incorporated herein by reference.

FIELD AND BACKGROUND OF THE PRESENT INVENTION

The present invention, in some embodiments thereof, relates to an optical resonance analysis system for analyzing reactions of chemical, biochemical, and/or biological materials and detecting properties of the above reactions. The present invention may be employed by types of optical resonance analysis systems in which light wave properties are measured as a function of angle of incidence, reflection, and or refraction. These optical systems include ellipsometry sensors, total internal reflectance (TIR) sensors, and SPR sensors, Brewster angle sensors.

Ellipsometry relies on the change of polarization of light waves reflected off a surface which is in contact with a specimen, to yield information about the specimen itself. Ellipsometry can probe the complex refractive index or dielectric function tensor, which gives access to fundamental physical parameters and is related to a variety of specimen properties, including morphology, crystal quality, chemical composition, or electrical conductivity.

In a standard ellipsometry analysis system, a light wave is emitted by a light source and is linearly polarized by a polarizer. The light wave illuminates a reflecting surface, which is in contact with the specimen, at an angle of incidence. The reflected light wave passes an optional compensator and a second polarizer, which is called analyzer, and falls into a detecting unit. The emitted and the reflected waves span the plane of incidence. Light waves, which are polarized parallel or perpendicular to the plane of incidence, are called p or s polarized, respectively. The detecting unit measures the ratio of the s-polarized and p-polarized components of the reflected light wave. Changes of this ratio give an insight upon the properties of the specimen.

Surface plasmons, are surface electromagnetic waves that propagate parallel along a metal-dielectric or metal-vacuum interface. Since the wave is on the boundary of the metal and the external medium, these oscillations are very sensitive to any change of this boundary, such as the absorption of molecules to the metal surface.

A typical SPR analysis system 100 is described in FIG. 1. A light wave 102 is emitted by a light wave source 104, polarized by a polarizer 106, refracted by a first surface 108 of a prism 110, before reaching a conductive layer 112—usually a layer of gold, silver, or aluminum, characterized by a thickness of about 50 nm—at an angle of incidence $\phi_i$. At conductive layer 112, some of the energy of light wave 102 is coupled to surface plasmons of conductive layer 112. Therefore, light wave 114, reflected at an angle of reflection $\phi_r$, by conductive layer 112, has a lower intensity than light waves 102. A detecting unit 116 receives reflected light wave 114, after light wave 114 exits a third surface 118 of prism 110, and measures the intensity of light wave 114. Conductive layer 112 is in contact with a specimen 120, usually a liquid or a gas, held within a specimen channel 121. Optionally, ligands 122 are placed on surface 124 of conductive layer 112. Ligands 122 hold target molecules 126 (also referred to as "analytes") to test the reaction of specimen 120 with target molecules 126. Changes within specimen 120—such as chemical, biochemical, and biological reactions—affect the behavior of plasmons, and the intensity measurement by detecting unit 116 is used to identify properties of specimen 120.

The energy lost by emitted wave 102 to the coupling with the surface plasmons depends on angle of reflection $\phi_r$. Generally, for waves of a given wavelength, the energy lost reaches a maximum at an angle, which is called "resonance angle". The amplitude of the resonance angle changes according to the properties of the specimen. Therefore, for a fixed wavelength, a comparison between the "intensity vs. angle of reflection" graphs of a specimen before and after a reaction, and observation of the shift of the graph over time of the specimen provide data on the reaction—such as association and disassociation rates. FIG. 2 shows "intensity (I) vs. angle of reflection ($\phi_r$)" graph for the specimen before the reaction (202), and the graph for the specimen after the reaction (204) The shift (206) between curve 202 and curve 204 is also shown. It is noted that $\phi_1$ is the resonance angle for the specimen before the reaction, while $\phi_2$ is the resonance angle for the specimen after the reaction of the specimen.

Total internal reflection (TIR) is an optical phenomenon that occurs when a light wave strikes a medium boundary at an angle larger than the critical angle with respect to the normal to the surface. If the refractive index is lower on the other side of the boundary no light wave can pass through, so effectively the whole wave is reflected, and an evanescent electromagnetic field is created at the boundary surface. The critical angle is the angle of incidence above which the total internal reflection occurs.

In a typical TIR analysis system, a light source emits a light wave that enters a prism through a first surface, and hits a second surface of the prism at an angle greater than the critical angle. At the second surface, therefore, total internal reflection is achieved, and an evanescent electromagnetic field is created. The light wave is reflected, but its polarization is changed. The second surface of the prism is in contact with a specimen to be assayed, and the properties of the specimen affect the polarization of the reflected light wave. The reflected wave exits the prism through a third surface, and reaches a detecting unit. The detecting unit receives the reflected light wave and measures the polarization of the reflected wave. Properties of the specimen are then calculated by relating the polarization values of the reflected wave to the angle of reflection. Optionally, the detecting unit measures the intensity of the reflected wave, and the properties of the specimen are calculated by an analysis of the total internal reflection step which characterizes a TIR "intensity vs. angle of reflectance" graph.

The Brewster angle is an angle of incidence at which p-polarized light, which illuminates a boundary between two media having different refractive indexes, is not reflected by the boundary. In a typical Brewster angle analysis system, a light source emits a light, which is polarized into p-state by a polarizer. The light illuminates a boundary between two media at angles close to the Brewster angle at which a specimen is introduced, and some of light is reflected toward a detector. Since the Brewster angle is sensitive to changes within the specimen, the polarization of the reflected light is affected by the changes of specimen. The detector measures the polarization of the reflected wave, in order to detect properties of the specimen.

The above systems are largely used in chemistry, biology, and biochemistry, as they are very sensitive to changes in specimens, which makes them suitable for measuring properties of reactions. In the above analysis systems, the reflective surfaces in contact with the specimen may be divided into a plurality of sensing areas, each sensing area in contact with a different specimen. This may allow the analysis systems to perform measurements on a plurality of specimens in a short time. For such a system to be effective, the detector is typically configured to take measurements of light waves characterized by different angles of reflection.

In U.S. Pat. No. 5,327,225 by Bender et al., disclosing a surface plasmon resonance sensor, reflected light from the conductive layer is guided to the detector by a wave guide. In U.S. Pat. No. 6,111,652 by Melendez et al., disclosing a high throughput apparatus for determining interaction properties of test entities, the detector has a large surface for receiving light waves at different angles of reflection. In U.S. Pat. No. 7,218,401 by Iwata et al., disclosing a surface plasmon sensor, a plurality of light detection means is provided, and each one of the detection means is positioned to receive light waves at a predetermined reflective angle. In U.S. Pat. No. 5,035,863 by Finlan et al., disclosing a sequencing apparatus, means for moving the detector are provided in order to enable the detector to take measurements of light waves characterized by different angles of reflection.

U.S. Pat. No. 7,057,720 by Caracci et al., which discloses an optical interrogation system and method capable of generating light beams that have desired optical properties which are directed towards a specimen array, a mask is provided. The mask is located between the detector and the specimen unit, and blocks predetermined light beams reflected from selected specimens in the specimen unit. However, this mask prevents the system described in the invention from assaying different specimens simultaneously.

U.S. patent application Ser. No. 11/274,923 by Takayama et al., discloses an analysis apparatus for analyzing samples by means of detecting lights from a plurality of spots formed on an analysis chip so as to hold the samples. The system includes a selectively light-transmitting unit for transmitting lights selectively from desired spots on a specimen unit to a light-sensitive detector. However, this selectively light-transmitting unit does not allow simultaneous analysis of a plurality of light waves coming from a plurality of areas in the specimen unit.

U.S. Pat. No. 6,873,417 by Bahatt et al. discloses an optical resonance analysis system, which optionally includes an optical system to focus different wavelengths to different areas of the detector.

SUMMARY OF THE PRESENT INVENTION

The present invention, in some embodiments thereof, relates to a system for analyzing properties—such as reaction constants, rates, and equilibrium—of chemical, biochemical, and biological reactions, optionally at multiple sites simultaneously, optionally in real time, by illuminating the reaction sites simultaneously with light at a plurality of angles of incidence, and analyzing a reflection and/or refraction of the illuminating light. Exemplary embodiments of the present invention may be employed by various types of optical measurement systems in which light wave properties are measured as a function of illumination angle, especially for chemical and biological processes. These optical systems include total internal reflectance systems, ellipsometry systems, Brewster's angle systems, and surface plasmon resonance (SPR) systems There is provided in accordance with an exemplary embodiment of the invention, an optical resonance analysis system, comprising:

at least one light source which emits an illumination at a plurality of angles;

a specimen unit which holds at least one specimen and configured for facilitating interaction between said specimen and said illumination, said interacting including one or both of reflecting part of said illumination, and refracting part of said illumination;

a detection unit configured to detect at least part of said illumination after said interaction; and a selecting unit which selects only a portion of said interacted light, said portion representing interactions with light at a subset of said plurality of angles of said illumination and wherein said selecting unit is reconfigured for selecting at least a different one of said portions, at different times.

In an exemplary embodiment of the invention, said selecting unit selects at least one portion of said reflected illumination. Optionally or alternatively, said illumination illuminates at least one location of said specimen unit at a range of continuous angles of incidence. Optionally or alternatively, said range of continuous angles of incidence is produced by a diffuser associated with said light source. Optionally or alternatively, said illumination is not collimated. Optionally or alternatively, said light source is a high current light source. Optionally or alternatively, said light source is maintained in a stable illumination state for at least 1 second.

In an exemplary embodiment of the invention, said light source comprises:

an array of light emitting diodes (LEDs); and a diffuser which diffuses light from said LEDs.

In an exemplary embodiment of the invention, said light source comprises only a single light source.

In an exemplary embodiment of the invention, said specimen unit is divided into a plurality of analysis areas, each analysis area potentially containing a different specimen. Optionally, a plurality of specimens are analyzed simultaneously.

In an exemplary embodiment of the invention, said detecting unit further captures a spatially continuous image of said specimen unit as illuminated by said light source. Optionally, said continuous image is a two dimensional image. Optionally, the system comprises a processing unit associated with said detecting unit and which selects a plurality of non-contiguous sections of said two dimensional image for further processing.

In an exemplary embodiment of the invention, said selecting unit selects said portion, to select a substantially single angle of illumination of said plurality of angles.

In an exemplary embodiment of the invention, said selecting unit selects said portion, according to a wavelength of said portion.

In an exemplary embodiment of the invention, said selecting unit selects said portion in chosen time frames, according to at least one selected analysis pattern.

In an exemplary embodiment of the invention, said selecting unit and said detecting unit are synchronized, said detecting unit taking measurements only when portions selected by said selecting unit reach said detecting unit.

In an exemplary embodiment of the invention, said selecting unit determines an angular span of said substantially single angle.

In an exemplary embodiment of the invention, said selecting unit comprises an array of liquid crystal elements, wherein a transparency of each of said liquid crystal elements is controlled, for transmitting said portions to said detecting unit or for blocking said portions. Optionally, a degree of said transparency of each of said liquid crystal elements is controllable to decrease an intensity of said portions which are transmitted to said detecting unit. Optionally or alternatively, said transparency of each said liquid crystal element is controlled to provide a gradual change between an area which transmits said portions and adjacent areas which block said portions, in a manner which reduces at least some diffractive effects.

In an exemplary embodiment of the invention, said selecting unit is positioned about at a Fourier plane of lens used to image said reflecting surface onto said detector.

In an exemplary embodiment of the invention, said selecting unit comprises:

a plurality of shutters selectively controllable to selectively transmit said portion to said detecting unit.

In an exemplary embodiment of the invention, said selecting unit comprises a plurality of mirrors, configured to selectively convey said portion to said detecting unit. Optionally, said mirrors are selectively controlled to change an orientation thereof. Optionally or alternatively, at least one of said portions reaches said detecting unit, by being reflected toward said detecting unit by at least one of said mirrors.

In an exemplary embodiment of the invention, said selecting unit comprises:

a first mask having at least one aperture; and
a second mask having at least one aperture linear array of slits; and
a mask mover configured to move one or both masks such that said selecting depends on a an alignment of said masks. Optionally, said first mask comprises a circular array of slits. Optionally or alternatively, said second mask comprises a linear array of slits.

In an exemplary embodiment of the invention, the optical resonance analysis system is a surface plasmon resonance (SPR) analysis system, and said detecting unit is configured for measuring one or both of a light wave polarization and a light wave intensity.

In an exemplary embodiment of the invention, the optical resonance analysis system is a total internal reflectance (TIR) analysis system, and said detecting unit is configured for measuring one or more of a light wave polarization and a light wave intensity.

In an exemplary embodiment of the invention, the optical resonance analysis system is an ellipsometric analysis system, and said detecting unit is configured for measuring one or both of a light wave polarization and a light wave intensity.

In an exemplary embodiment of the invention, said optical resonance analysis system is a Brewster angle analysis system, and said detecting unit is configured for measuring one or both of a light wave polarization and a light wave intensity.

In an exemplary embodiment of the invention, a high-throughput screening system is provided including an optical resonance analysis system as described herein.

There is provided in accordance with an exemplary embodiment of the invention, a method for detecting at least one property of at least one specimen in an optical resonance analysis system, comprising:

illuminating a specimen with illumination light at a plurality of angles to provide modified light;
virtually selecting only a portion of said illumination light by selecting only a portion of said modified light, said selected portion of modified light corresponding to illumination light at only a subset of said angles; and
detecting a signal on said selected impinged light. Optionally, said selecting comprises:

selecting a plurality of different sets, each set comprising at least one portion, at different times. Optionally or alternatively, said selecting comprises selecting according to wavelength. Optionally or alternatively, the method comprises analyzing said detected signal to characterize at least one property of said specimen.

In an exemplary embodiment of the invention, the method comprises repeatedly selecting said portion for said analysis.

In an exemplary embodiment of the invention, said detecting comprises one or more of:

measuring an intensity of said portion; and
measuring a polarization of said portion.

In an exemplary embodiment of the invention, the optical resonance analysis system is a surface plasmon resonance (SPR) analysis system for high throughput screening.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the present invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings:

FIG. 6 is a schematic drawing illustrating a selecting element which includes a linear array of slits and mechanical shutters, according to some embodiments of the present invention;

DESCRIPTION OF SPECIFIC EMBODIMENTS OF THE PRESENT INVENTION

Figure 1:
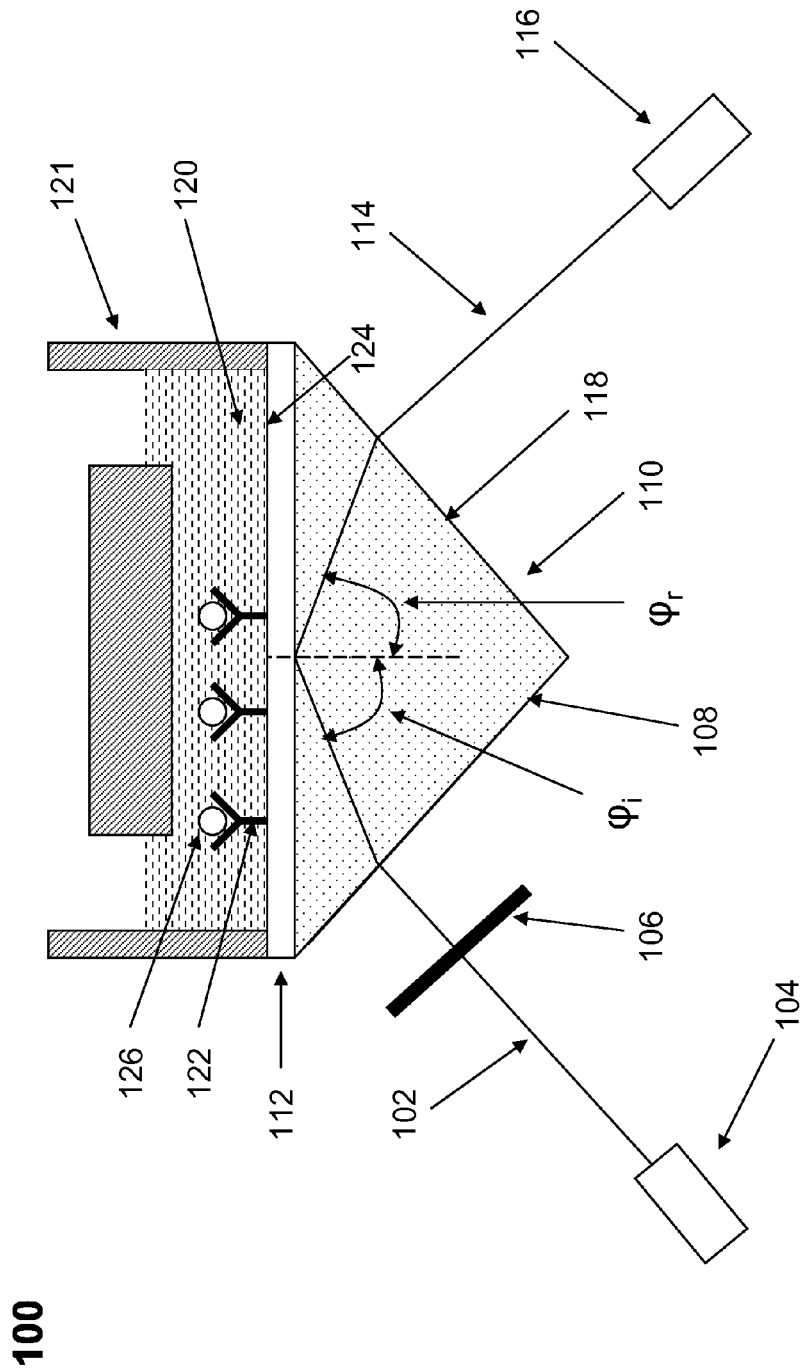
FIG. 1 is a schematic drawing illustrating a typical SPR measurement system, according to prior art.

The present invention, in some embodiments thereof, relates to an optical resonance analysis system for analyzing reactions of chemical, biochemical, and/or biological materials and detecting properties of the above reactions. The present invention may be employed by types of optical resonance analysis systems which rely on angle scanning of light wave properties. Examples of such optical resonance analysis systems include ellipsometry systems, total internal reflectance (TIR) systems, Brewster's angle systems, and surface plasmon resonance (SPR) systems.

According to some embodiments of the present invention, an optical resonance analysis system is provided for detecting properties of reactions of specimen with analytes. The system comprises a light source which emits light, which illuminates a reflective layer of a specimen unit at a plurality of angles of incidence, within a range $\Delta\phi_i$. The reflective layer is illuminated so that each of a plurality of locations of the reflective layer is illuminated at a continuous plurality of angles of incidence. The specimen unit contains at least one specimen to be analyzed. The illuminating light is reflected at a range $\Delta\phi_r$ of angles of reflection, by each of the plurality of the illuminated locations, and the reflected light reaches a receiving surface of a detecting unit, which is configured for measuring at least one property of the reflected light. Optionally, some of the light is refracted through the reflective layer and the specimen, and the detecting unit is positioned to measure at least one property of light refracted through the specimen.

It is a particular feature of some embodiments of the invention that instead of or in addition to illuminating with a source of a known angle of incidence, optical processing is employed to "select" a part of the illumination which corresponds to a virtual source with a known angle, after the light is reflected (or otherwise modified, such as by transmission) off the sample. Optionally or alternatively, other properties of the reflected light are modified after reflection and before detection, such as intensity.

It is a particular feature of some embodiments of the invention, that there is more flexibility with respect to the illumination as it may not be required to switch on and off and/or to operate at a restricted range of angles. Optionally, the illumination provides light at a continuous and wide range of angles. Optionally, the illumination provides light as a plurality of spatially discrete sources and/or at a plurality of angular ranges.

According to some embodiments of the present invention, the optical resonance analysis system is characterized by a selecting unit placed between the reflective layer and the detecting unit. The selecting unit selects one or more portions of light waves of the reflected light which correspond to light that originated form a relatively small range of angles from the illumination before interacting with the sample. Optionally, the selecting unit selects portions, according to a frequency range by which the portions are characterized. Of the portions that are selected according to angle of reflection, each portion is characterized by a span $d\phi_r$ of angles of reflection. Span $d\phi_r$ is less than range $\Delta\phi_r$, and the magnitude of span $d\phi_r$ is determined by characteristics of the selecting unit.

Figure 2:
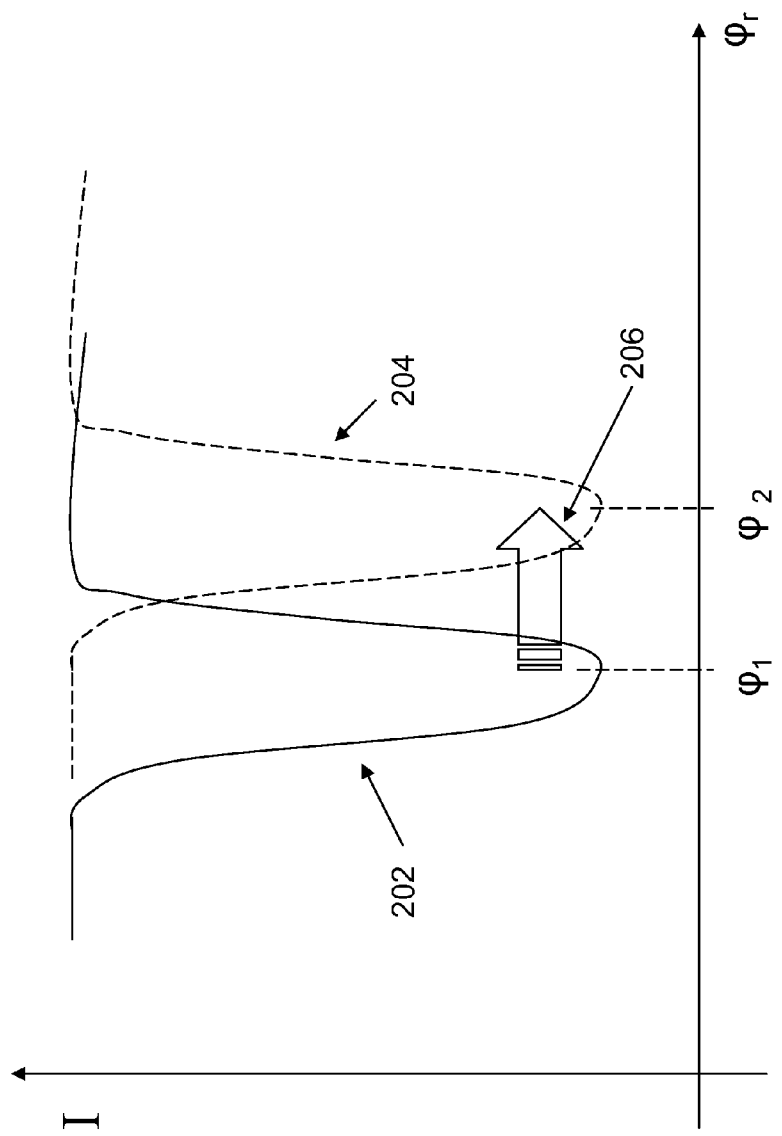
FIG. 2 is a typical "intensity vs. angle of reflection graph", generated by SPR measurements, according to prior art.

The detecting unit measures at least one property of each portion reaching the detecting unit. In use, the selecting unit optionally operates in cycles. Each cycle, the selecting unit allows a different set of one or more portions to reach the detecting unit. The selecting unit has a configurable and/or movable portion that allows it to vary, optionally sequentially, the one or more portions of light which are allowed to reach the detecting unit. The measured property may then be plotted as a function of angle of reflection, as shown in FIG. 2, and the plot allows a calculation of properties of the reaction. Optionally or alternatively, the measured property is analyzed to yield a graph indicating a displacement of the measured property from a baseline, as a function of time.

In an exemplary embodiment of the invention, additional accuracy is provided by repeating the above cycle a plurality of times and applying an averaging function.

Optionally, one specimen is analyzed by the above system. Optionally, the reflective layer is divided into a plurality of sensing areas, each sensing area being in contact with a reaction of the same specimen with a different analyte, or with a reaction of different specimens altogether. Each sensing area is also illuminated by light at a plurality of angles of incidence, and reflects light at a plurality of angles of reflection. This embodiment enables the system to assay a plurality of reactions in a short period. Optionally, a plurality of regions are imaged simultaneously, for example, using a 1D or 2D imager, each snapshot of such an imager with respect to a position of the selecting unit reflecting a different light source angle and/or frequency. Optionally, the selecting unit simultaneously selects a plurality of spaced apart illumination portions.

According to some embodiments of the present invention, the optical resonance analysis system further includes an illumination control apparatus, which controls at least one property of the illuminating light before the illuminating light reaches the reflective layer According to some embodiments of the present invention, a method is provided for detecting properties of reactions of specimen, through an optical resonance analysis system.

The selecting unit controls the magnitude of the spans characterizing the portions which reach the detecting unit, and may set these spans to be very small. For example, a selecting unit may reduce the magnitude of the angular spans of the portions, by transmitting the portions to the detecting unit through an aperture measuring 1.5 mm; for some lens arrangements, setting the span size to be about 0.1°. Apertures at which embodiments of the present invention are known to work may be as small as 0.2 mm and 0.3 mm, for some lens arrangements, setting the angular span size to be about 0.05°. Narrow spans may reduce cross-talk between different reaction sites on the specimen unit, as scattered light is blocked and does not reach the detecting unit. Optionally or alternatively, other span sizes (angular sizes of a virtual source) may be provided, for example, between 0.05° and 3°, depending, for example, on the design of the selecting unit, lens used and imager.

In an exemplary embodiment of the invention, the span of angular range of the emitted light is related to the resonance effects that are to be measured and to the desired sensitivity. For example, if an SPR effect is limited to a portion of reflection angles of about 2°-3° and a sampling of, for example, 5, 10, 20, 30 or more samples within this range are desired, it may be desirable to have an angular span of the selected portions of 0.1°, or 0.2°. The illumination source may illuminate, for example, at a range of angles encompassing, 5°, 10°, 20°, 30° or more.

Because reflected light is assayed in portions characterized by narrow spans of angles of reflection, the angle of the detected light need not be determined by the illuminating side of the system. Therefore, the light source does not need to emit a high quality collimated beam of illuminating light, such as a laser beam, and lower quality light sources may be used without an increase of signal-to-noise ratio, and without a loss of measurement sensitivity. Optionally, the illumination light is unstructured light. Optionally, the illuminating light is not collimated. An example of lower quality light source is a light emitting diode (LED), or an array of LEDs. According to some embodiments of the present invention, the light source is a plurality of LEDs, covered by a diffuser. Such a light source illuminates the specimen unit at a large range of angles of incidence, thereby increasing the range of angles of reflection. This allows larger shifts of the "light property vs. angle of reflection" curve to be measured, and increases a dynamic range of the optical resonance analysis system.

In an exemplary embodiment of the invention, a larger selection of light source types and/or designs may be included within an optical resonance analysis system. For example, high current power sources may be used. High current light sources that may be used in embodiments of the present invention, include, for example, light sources characterized by a power of, 2 W, 5 W, 10 W, 20 W, 40 W, 80 W or more.

In an exemplary embodiment of the invention, use is made of the selection of virtual light sources after the fact, to reduce the need to switch the source on and off throughout the analysis process, in order to scan and analyze different areas and/or angles of the specimen unit. In an exemplary embodiment of the invention, leaving the light on for a period of time reduces artifacts associated with turning the source on and off, such as source temperature and illumination intensity fluctuations and/or source stability and/or repeatability over time. Optionally or alternatively, leaving the source on allows the use of higher current without associated high-current fast switches and/or without associated electrical noise caused by such switching. In some embodiments of the present invention, the time between switching of light sources may be one or more of about 1-5 seconds, about 1-5 hours, about 1-5 days, and/or intermediate or greater times. Optionally, stable illumination is obtained for periods of seconds, hours, days, weeks or longer according to a user's preference and needs of the optical resonance analysis system.

In an exemplary embodiment of the invention, because the areas of the specimen unit that are to be analyzed can be illuminated constantly, for example, throughout the whole analysis process, the above areas are uniformly heated by the illumination, and artifacts caused by the difference in temperature of the analyzed specimens is reduced. Also, when such heating effects are more stable, the temperature of the analyzed areas may be more easily controlled, for example, by being uniformly cooled by cooling fluids.

In an exemplary embodiment of the invention, because the light source need not be switched on and off during analysis, a larger range of light sources may be practically used, including light sources characterized by a high current and which are not amenable and/or stable under fast switching. High current light sources emit light that is more stable in wavelength and intensity, and have higher signal-to-noise ratio. Furthermore, high current light source may be set to emit light at higher intensities. Since light intensity increases more quickly than shot noise does, the signal-to-noise ratio may be further increased. For example, light intensity may be around $400 \times 10^{11}$ photons per area of interest per second, where each area of interest includes around 2000 pixels on the receiving surface of the detecting unit. The above intensity is about 100 times larger than light intensities currently used in the field. In other embodiments, the intensity is, for example, 5%, 10%, 25%, 50%, 120%, 200% or smaller or intermediate or greater percentages of the above intensity.

High current light sources are, for example, single light sources, such as large LED dies. When the specimen unit is illuminated by a single light source, a property—for example intensity (or frequency)—of a portion of the emitted light that does not illuminate the specimen unit may be measured at high accuracy. The measured value is then optionally used to normalize the values of the same property measured by the detecting unit as a function of angle of reflection and/or to control the light source. This normalization can increase the sensitivity of the system, by correcting for as some instabilities and fluctuations in the light source. The normalization is typically harder to perform if the light source is an array of low-current light sources, since instabilities in different light sources may happen at different times and in different ways, and are therefore hard to detect.

Another characteristic of an optical resonance analysis system, characterized by a light source which is not switched on and off, is that one can trade off analysis speed and data collection quality, which can proves useful when reactions happen quickly. While it may be possible with a switched source, this may practically require switching the switched source at a speed higher than it is capable of.

Figure 3A:
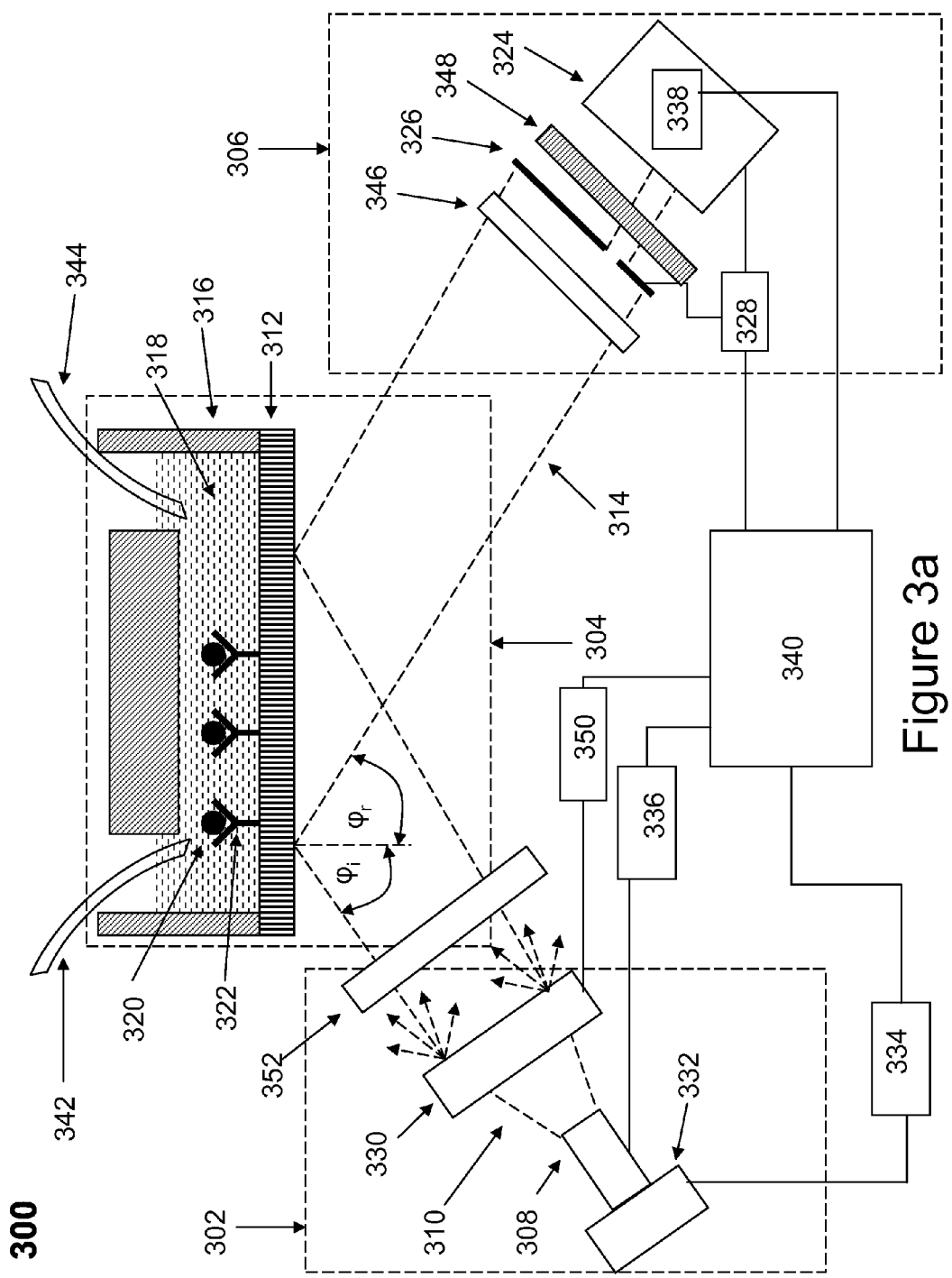
FIGS. 3a, 3b and 3c are schematic drawings illustrating an optical resonance analysis system for measuring properties of a reaction, according to some embodiments of the present invention.

Referring now to the drawings, FIG. 3a is a schematic drawing illustrating an optical resonance analysis system 300 for measuring properties of a reaction, according to some embodiments of the present invention.

Optical resonance analysis system 300 includes an illumination subsystem 302, a specimen unit 304, and a detecting subsystem 306. Illumination subsystem 302 includes a light source 308 for emitting an illuminating light 310 which illuminates a plurality of locations of specimen unit 304, each location being illuminated at an optionally continuous angular range $\Delta\phi_i$ of angles of incidence $\phi_i$. Illuminating light 310 is optionally a converging or a diverging illumination. Optionally, illuminating light 310 is monochromatic. Alternatively, illuminating light is characterized by a range of wavelengths. Optionally angular range $\Delta\phi_i$ is set to about 2°. Optionally $\Delta\phi_i$ is set as high as 20°. Optionally, illuminating light 310 is uncollimated and/or otherwise unstructured. Optionally illuminating light 310 is a structured, collimated beam of light. Optionally, a monochromator 352 is provided for filtering light within a narrow range of wavelengths. Though monochromator 352 is shown in FIG. 3a to be located before specimen unit 304, monochromator 352 is optionally positioned anywhere in system 300, for example, before detecting sub-system 306. Optionally or alternatively, a plurality of frequency-specific light sources are used and optionally switched as needed.

Specimen unit 304 includes a reflective layer 312, and a specimen holder 316. Reflective layer 312 is configured for being illuminated by illuminating light 310 and generating, at a plurality of illuminated locations, a reflected light 314, characterized by a range $\Delta\phi_r$ of angles of reflection $\phi_r$. Specimen holder 316 is in contact with a surface of reflective layer 312, and is configured for housing at least one specimen 318 and at least one analyte 320, which reacts with specimen 318. Specimen holder 316 is optionally a flow cell, through which one or more specimens 318 may be conducted during the analysis process, according to a user's requirements. Optionally, specimen holder 316 is a cuvette, the contents of which may be changed by a user only before or after the analysis. Optionally, specimen holder 316 is an array of flow cells filled according to the method featured in U.S. patent application Ser. No. 10/578,860 by Notcovich et al., the disclosure of which is incorporated herein by reference and is configured to hold 36 or 64 different specimens. In an exemplary embodiment of the invention, holder 316 includes an upper layer and a lower layer, with a plurality (e.g., 6) channels formed in one of the layers. After a first material is flowed along the channels, one layer is lifted up and rotated 90° so that further flowing along the channels will create intersection points (e.g., 36) between the original flow and the new flow. Optionally, areas between the intersections are used for calibration purposes. Specimen 318 is also in contact with a surface of reflective layer 312. Optionally, analyte 320 is secured to a surface of reflective layer 312 by ligands 322.

A plurality of locations of reflective layer 312 are illuminated by illuminating light 310 at a range of angles of incidence between a maximal angle of incidence $\phi_{MAX}$ and a minimal angle of incidence $\phi_{MIN}$. $\Delta\phi_i$ is defined to be the difference between $\phi_{MAX}$ and $\phi_{MIN}$, while $\phi_{AVGi}$ is defined to be the average of $\phi_{MAX}$ and $\phi_{MIN}$. All light waves of illuminating light 310 are therefore characterized by angles of incidence within the range between ($\phi_{AVGi}-\Delta\phi_i/2$) and ($\phi_{AVGi}+\Delta\phi_i/2$). Similarly, all light waves of reflected light 314 are characterized by angles or reflection with the range between ($\phi_{AVGr}-\Delta\phi_r/2$) and ($\phi_{AVGr}+\Delta\phi_r/2$), where $\phi_{AVGr}$ is a central angle of reflection, and $\Delta\phi_r$ is the difference between a maximal and minimal angles of reflection. According to some exemplary embodiments of the present invention, $\Delta\phi_i$ and $\Delta\phi_r$ ranged between 1° and 40°, for example, between 2° and 20° or between 5° and 18°.

Detecting subsystem 306 includes a detecting unit 324, which takes measurements of at least one property of light waves in reflected light 314. According to some embodiments of the present invention, detecting subsystem 306 further includes a selecting unit, which includes a selecting element 326, optionally controlled by a selecting controller 328, for selecting portions of reflected light 314, and directing the selected portions toward detecting unit 324. Each portion is centered around a different angle of reflection and is characterized by an angular span $d\phi_r$, smaller than $\Delta\phi_r$. Therefore, a portion defined by angle of reflection $\phi_k$ and span $d\phi_r$ includes light waves of reflected light 314 characterized by angles of reflection within a sub-range between ($\phi_k-d\phi_r/2$) and ($\phi_k+d\phi_r/2$). Optionally, selecting element 326 is controlled by selecting controller 328 to filter selected portions, so that the selected portions reach detecting unit 324 in selected time frames and/or according to predefined and/or dynamic analysis pattern. According to some exemplary embodiments of the present invention, $d\phi_r$ is between 0.075° and 1°.

Optionally, detecting unit 324 includes a processing subunit 338, for processing and analyzing the data collected by detecting unit 324 and calculating the properties of the reaction or reactions, accordingly. Optionally processing subunit 338 is a field-programmable gate array (FPGA). Optionally, processing subunit 338 selects only portions of the acquired image for further processing, as relating to areas of the image that represent sample regions and/or reference regions. Optionally, processing subunit 338 is separate from detecting unit 324. Optionally, the calculation of the reaction properties is performed according to a graph in which a property of the light waves is plotted as a function of angle of reflection, for example as shown in FIG. 2. Optionally, processing unit 338 (or another processing unit, for example a PC) analyzes data through an algorithm which fits a curve. Optionally, the output of the sampling process is a curve of intensity as a function of angle. Optionally, this curve is defined functionally using one or more parameters. Optionally, unit 338 fits the actual curve to an expected curve and indicates the change in one or more parameters that define the curve and which are needed for the matching. Optionally, detecting subsystem 306 includes a frontal optical apparatus 346 and a rear optical apparatus 348, both including optical elements and/or devices, such as polarizers, collimators, and lenses, for adjusting the properties of reflected light 314 and/or of the portions of reflected light 314 that reach detecting unit 324.

Optionally, according to some embodiments of the present invention, illumination subsystem 302 includes an illumination control apparatus (not shown). Optionally, the illumination control apparatus includes one or more of an optical control sub-apparatus 330, a temperature control sub-apparatus 332, and a source control sub-apparatus 336. Optical control sub-apparatus 330 manipulates illuminating light 310 before illuminating light 310 reaches specimen unit 304, and controls at least one of its properties. Optionally, optical control sub-apparatus is controlled by optical control unit 350.

The temperature of the light source affects at least one property of the illuminating and reflected light, for example intensity. Therefore, a constant temperature of the light source for a length of time results in a constant intensity of the beams for that same length of time. On the detecting side, a constant temperature of the light source means less noise and a higher sensitivity in intensity measurements. Therefore temperature control sub-apparatus 332 sets the temperature of light source 308 and optionally keeps the temperature constant throughout the analysis, thereby potentially increasing the measurement sensitivity and/or accuracy of system 300.

Optionally temperature control sub-apparatus 332 is controlled by a temperature control unit 334. Source control sub-apparatus 336 controls the operation of light source 308, for example by setting the intensity and/or wavelength of illuminating light 310.

Optionally, a central user interface 340 is connected to the illumination control apparatus, for allowing a user to select and/or adjust one or more properties of illuminating light 310. Optionally, central user interface 340 coordinates the operation of the different parts of the illumination control apparatus. Optionally central user interface is also connected to selecting controller 328, and processing subunit 338, in order to control the selecting and detecting of portions of reflected light 314, according to a predefined and/or dynamic analysis pattern set according to the properties of illuminating light 310.

Optionally, optical system 300 is used as one of a SPR analysis system, a TIR analysis system, a Brewster angle analysis system, and an ellipsometric analysis system. Optionally, reflective layer 312 is divided into a plurality of sensing areas; each sensing area is in contact with a different flow channel. Optionally, each flow channel contains a different analyte 320, which is configured to react with one specimen, and therefore each flow channel houses a different reaction of the same specimen. Optionally, each flow channel contains a different analyte 320, each analyte 320 configured to react with a different specimen and therefore each flow channel houses a reaction of a different specimen. Each sensing area reflects a plurality of portions of illuminating light 310, and each of these portions is assayed by detecting unit 324. This embodiment allows the construction of curve of a light wave property—for example, intensity—as a function of angle of reflection, for each sensing area, and therefore allows system 300 to simultaneously detect properties of a plurality of reactions.

Optionally, system 300 further includes a specimen delivery apparatus 353(shown in FIG. 3c) connected to reservoirs 355 of different specimens. The specimen delivery apparatus is configured for delivering specimens selected by a user to specimen holder 316. The specimen delivery apparatus includes a specimen inlet 342 for delivering specimen 318 from a reservoir into specimen holder 316, and a specimen outlet 344 for emptying specimen holder 316 of its contents. Optionally, the specimen delivery apparatus is manually operated, or automated and controlled by a specimen control unit (not shown) or a combination of the two.

Optionally, the specimen delivery apparatus includes a robotic unit for the manipulation of samples. Optionally the specimen delivery apparatus places a plurality of specimen upon a surface of reflective layer 312, according to the method featured in U.S. patent application Ser. No. 10/578, 860 mentioned above. Optionally, the specimen delivery apparatus is also connected to central user interface 340. Optionally, central user interface 340 coordinates the operation of many parts of system 300 and system 300 is optionally partially or fully automated. In an exemplary embodiment of the invention, system 300 performs a quick analysis of a plurality specimens, and optionally using automation, system 300 is configured for performing a high throughput screening of a plurality of specimens.

Optionally, the specimen delivery apparatus includes tubing that includes one or more valves, check valves, pumps, and degassers. Optionally, the part of the specimen delivery apparatus that is attached to the flow channel is made out of a flexible material such as Polydimethylsiloxane (PDMS) and silicon rubber. Optionally, specimen container 316 is temperature controlled and stabilized, in order to improve signal stability and to perform analysis at different temperatures.

Optionally, the specimens may also be held at selected temperatures by placing specimen reservoirs at a temperature controlled zone.

Optionally, more than one light source 308 is provided. Optionally an array of light sources is provided. Optionally light source 308 includes one or more of LEDs, diode lasers, sulfur lamps, incandescent bulbs, arc lamps, discharge lamps, lasers and/or any combination thereof. Optionally, light source 308 is an array of LEDs working together, covered by a diffuser. Such a light source covers a large area and acts like a single light source, because of the presence of the diffuser. Optionally, the light source is not continuous (e.g., it is an array of sources, optionally with a light homogenizer and/or reflectors, but alternatively without a diffuser or a single source with some spatial masking). The selecting element as described herein is optionally used to select a spatial subset of the light sources and may operate even if the illumination is spatially disjoint.

Optionally, light source 308 is movable, and may be tilted, in order to control the intensity of the part of light 310, which illuminates reflective surface 312, without changing the driving of source 308. Optionally or alternatively, the light source is tilted to increase the uniformity of illumination at various angles.

Optionally, detecting unit 324 includes a single detector that quantifies the intensity of delivered electromagnetic radiation, for example a silicon photodiode, a photomultiplier, and/or an avalanche photodiode. Optionally, detecting unit 324 is a single detector that measures the polarization of electromagnetic waves, such as detectors commonly used in TIR analysis systems, ellipsometry analysis systems, and Brewster angle analysis systems. Optionally, detecting unit 324 is a linear array of detectors such as a line scan camera, or multiple combinations of line scan detectors. Optionally, detecting unit 324 is a two dimensional detector, for example a charge coupled device (CCD) based sensor, or a complementary metal oxide semiconductor (CMOS) based sensor. Optionally, detecting unit 324 includes any combination of the above types of detectors. According to some embodiment of the present invention, detecting unit 324 includes a CMOS detector, which is able to take measurements at a speed of 500 frames per second. Optionally, the system is configured so that the imager operates at near saturation (e.g., for the expected signals) thereby possibly minimizing shot noise effects. A fast detecting unit 324 can increase the analysis speed of system 300.

Figure 3B:
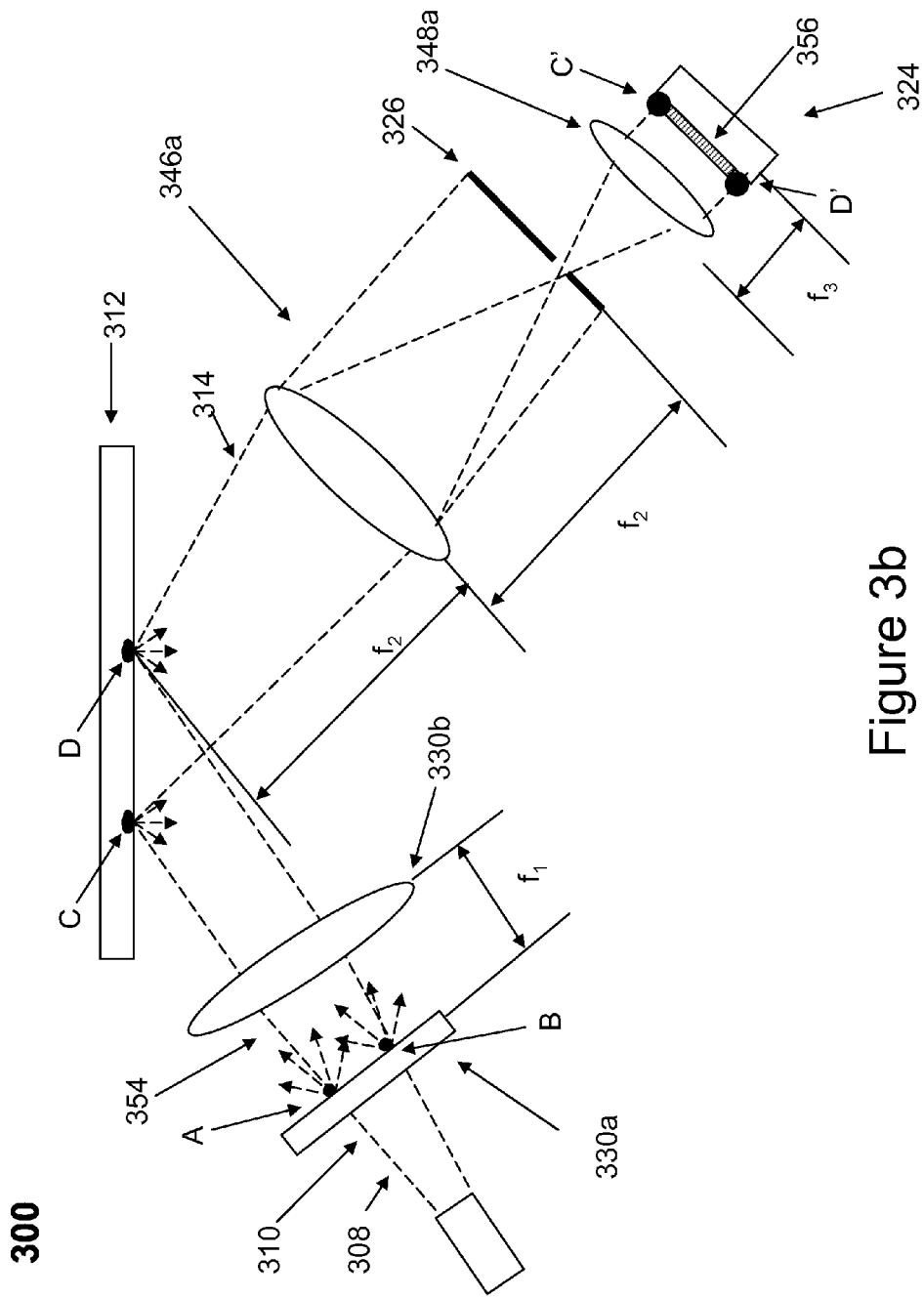
Figure 3C:
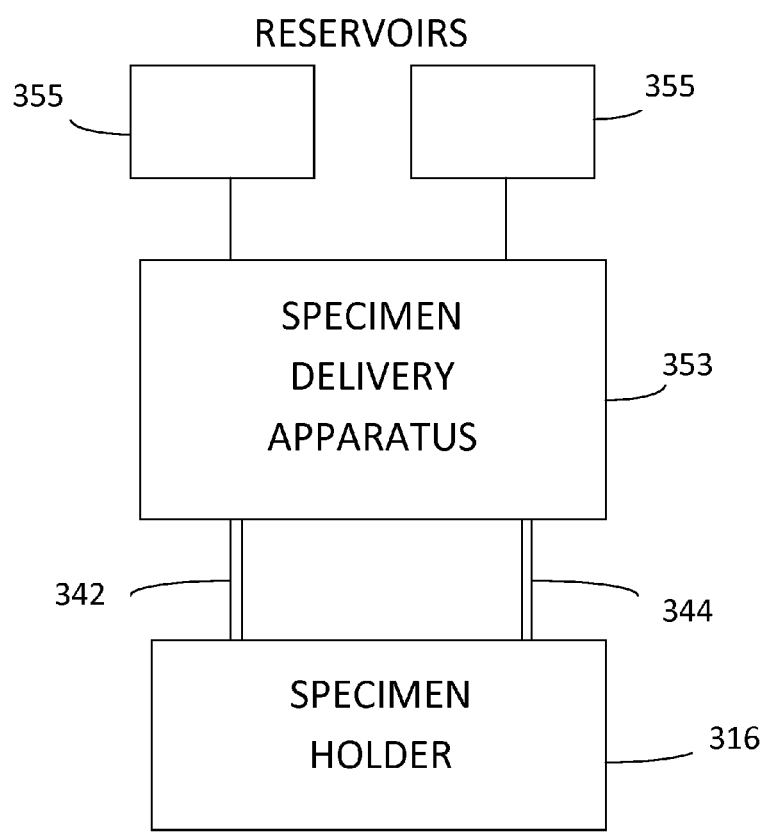

FIG. 3b is a schematic explanation of a specific implementation, using imaging and aperture-type selection, of the system shown in FIG. 3a.

In FIG. 3b, optical control sub-apparatus 330 is substituted by a diffuser 330a and a positive lens 330b, which are included in optical control sub-apparatus 330. Frontal optical apparatus 346 is substituted by a frontal lens 346a, and rear optical apparatus is substituted by a rear lens 348a. Selecting element 326 is optionally characterized by an aperture, through which light is transmitted toward detecting unit 324.

Lens 330b has a focal length $f_1$ and is located at a distance of about $f_1$ away from diffuser 330a. Optionally, lens 330b is located at a distance of exactly $f_1$ away from diffuser 330a. Frontal lens 346a has a focal length of $f_2$ and is located at a distance of about $f_2$ away from selecting element 326, and at a distance of about $f_2$ from reflective layer 312. Optionally, frontal lens 346a is located at a distance of exactly $f_2$ away from selecting element 326. Optionally, frontal lens 346a is located at a distance of exactly $f_2$ away from reflective layer 312. Rear lens 348a has a focal length of $f_3$ and is located at a distance of about $f_3$ away from a receiving surface of detecting unit 324. Optionally, rear lens 348a is located at a distance of exactly $f_3$ away from a receiving surface of detecting unit 324. Optionally, rear lens 348a is positioned at a distance having the same order of magnitude as $f_3$ from selecting element 326. Optionally, 348a is positioned at a distance of exactly $f_3$ from selecting element 326.

Light 310, is emitted by light source 308, and diffused by diffuser 330a. At diffuser 330a, a plurality of virtual light sources is created. Two exemplary virtual light source A and B are shown in FIG. 3b. Diffused light 354 reaches lens 330b and is directed towards a surface of reflective layer 312, and illuminates reflective layer 312 at a plurality of locations. Lens 330b collects light waves which would not normally reach reflective layer 312, and directs them to reflective layer 312. Lens 312 optionally acts as a collimator. Optionally, lens 330b converges diffused light 354. Optionally, the system of FIG. 3b does not include lens 330b. Each location is illuminated by a plurality of angles of incidence and reflects light at a plurality of angles of reflection. Two exemplary locations, C and D, are illuminated. Optionally each location is illuminated by light from both virtual light sources A and B.

Reflected light 314 is refracted by frontal lens 346a, and optionally converged, so that all light waves of reflected light 314 fall onto a surface of selecting element 326. In an exemplary embodiment of the invention, selecting element 326 is positioned at the back of a focal plane of lens 346a, where a virtual image of the source is formed. Optionally, selecting element 326 is positioned at the back of the Fourier plane of lens 346a.

Selecting element 326 selects light waves from reflected light 314 to be transmitted toward detecting element 324. In an exemplary embodiment of the invention, the selection comprises selecting only light which was incident on layer 312 at a particular sub-range of angles. This sub-range corresponds to a particular virtual light source A (or B). Before reaching the receiving surface of detecting unit 324, the selected light waves are converged by rear lens 348a, so that an image of reflective layer 312, convoluted with the "selected" virtual source is created on the receiving surface of detecting unit 324. Images C' and D' of locations C and D, as illuminated by virtual sources A and B, are created. In some embodiments, selecting element 326 can simultaneously select a plurality of spatially disjoint light sources, for example, including a plurality of slits, each corresponding to a different angular range.

Detecting unit 324 measures a property of the light (e.g., intensity) which reaches detecting unit 324 and optionally captures an image of a selected location on the illuminated surface of reflective layer 312.

Optionally, lens 330a, frontal lens 346a, and/or rear lens 348a may be replaced by other light manipulation and/or imaging elements, such as a Fresnel zone lens, a spherical reflector, a parabolic reflector, an amorphous lens, or a cylindrical lens.

According to some embodiments of the present invention, light 310 is monochromatic, and selecting element 326 is a diffractive element, for example a diffraction grating, which transmits waves of selected diffraction numbers toward detecting unit 324 in order to create an image 356 of light source 308 illuminating the reflective layer 312, on a receiving surface of detecting unit 324. In this embodiment frontal lens 346 is optionally not used or is elsewhere positioned.

In some embodiments, it may be desirable to tilt one or more of detecting unit 324, frontal lens 346a, and rear lens 348a, at angles determined by using the Scheimpflug construction rules. This may support an adequate imaging of locations upon the illuminated surface of reflective element 312, which may be imaged from an angle which is far from being perpendicular to the reflective element. Optionally or alternatively, the detector is curved to better correct for such non-perpendicular effects. Optionally or alternatively, intensity effects are corrected for during a calibration procedure.

In an exemplary embodiment of the invention, selecting element 326 is a light collimator which accepts light only from a certain sub-range of angles. Optionally, the range is changed by controlling and/or rotating such a collimator. Optionally, such a collimator need not be positioned near a Fourier plane of the detection system.

Optionally or alternatively to selecting light from an illumination source after that light is modified by a sample, light is selected (e.g., with a selecting element or mask) before it interacts with the specimen.

Figure 4A:
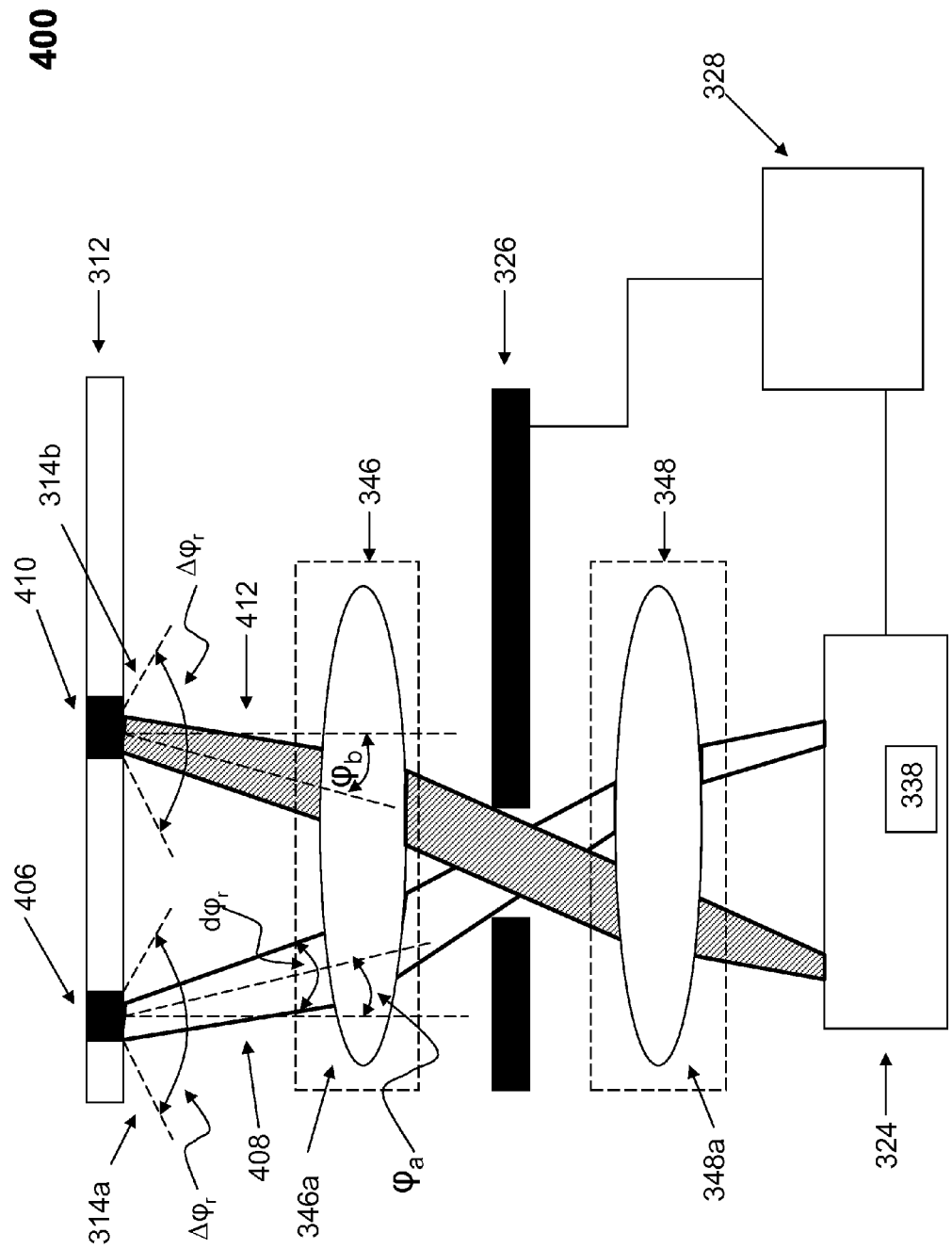
FIGS. 4a and 4b are schematic drawings illustrating in detail a detecting subsystem belonging to the system depicted in FIG. 3, according to some embodiments of the present invention.
Figure 4B:
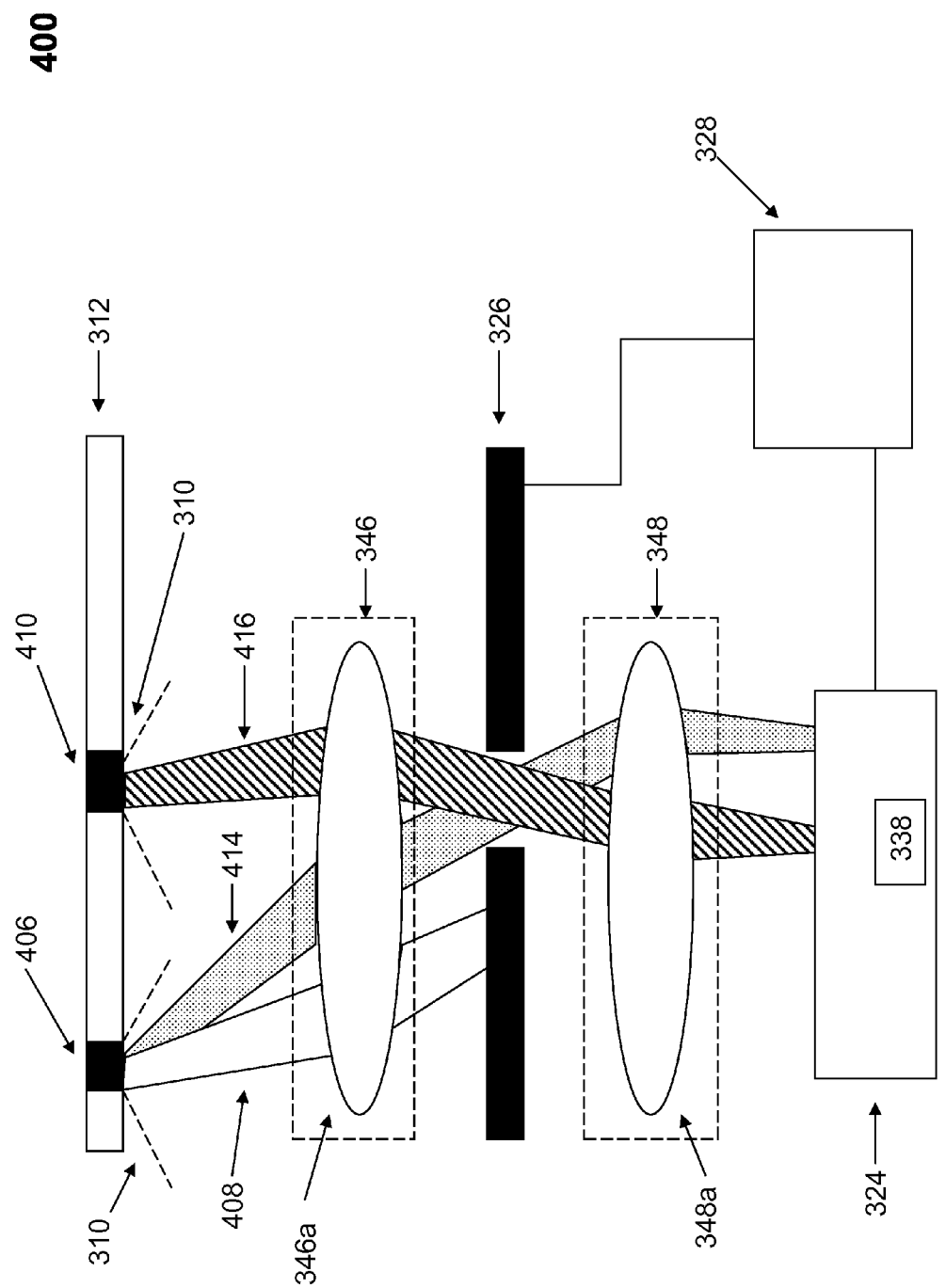

FIGS. 4a and 4b are schematic drawings illustrating in detail a detecting subsystem belonging to the system depicted in FIGS. 3a and 3b, according to some embodiments of the present invention. Optionally, this allows the use of a stable light source as described herein.

Detecting subsystem 400 is an exemplary subsystem, which may be substituted to detecting subsystem 306 shown in FIGS. 3a and 3b. Detecting subsystem 400 includes detecting unit 324, selecting element 326, selecting controller 328, and processing subunit 338, all of which have been described above. Optionally, frontal optical apparatus 346 is a frontal lens 346a or an array of lenses, and rear optical apparatus 348 is a rear lens 348a or an array of lenses.

In FIG. 4a, an area 406 of reflective layer 312 showed in FIG. 3 reflects illuminating light 310, thereby generating reflected light 314a characterized by a range $\Delta\phi_r$ of angles of reflection, as defined above. Reflected light 314 encounters frontal lens 346a, which converges light waves of reflected light 314, in order to ensure that all light waves of reflected light 310 reach a surface of selecting element 326. This converging takes place so that all light waves in reflected light 314 reach detecting unit 324 and no data is lost from any light waves or any portions of reflected light 314a. Also, without the converging, some unwanted light waves or portions may reach detecting unit 324 and produce noise and/or cause measurement errors. According to a preferred embodiment of the invention, selecting element 326 has a surface parallel to the plane of frontal lens 346a. According to an embodiment of the invention, selecting element 326 has a surface located around a focal length of frontal lens 346a.

At the surface of selecting element 326, some of reflected light 314a is blocked by selecting element 326, and a portion 408 passes through an aperture of selecting element 326. Portion 408 is characterized by an angular span $d\phi_r$, and is centered around angle of reflection $\phi_a$. Portion 408 then encounters rear lens 348a, which directs portion 408 to a receiving surface of detecting unit 324. According to a preferred embodiment of the invention, detecting unit 324 has a receiving surface parallel to the plane of rear lens 346a. According to a preferred embodiment of the invention, detecting unit 324 has a receiving surface located around a focal length of rear lens 346a. A measurement of at least a property of portion 408 is performed by detecting unit 324.

Another area 410 of reflective element 312 reflects illuminating light 310, thereby generating reflected light 314b, characterized by a range $\Delta\phi_r$ of angles of reflection. A portion 412 is characterized by angular span $d\phi_r$ and centered around angle of reflection $\phi_b$. Portion 412 is the only portion of light reflected by area 410 to reach detecting unit 324.

In FIG. 4b, selecting element 326 is moved and/or reconfigured, optionally by selecting controller 328, so that the aperture of selecting element 326 is located at a different place. Therefore, portion 414 reflected by area 406, and portion 416 reflected by area 410 pass through the aperture and reach detecting unit 324.

Optionally, detecting unit 324 includes a single detector and is therefore able to detect only one portion for each configuration or position of selecting element 326, since only one portion falls onto a receiving surface detecting unit 324. According to this option, selecting element 326 is moved and/or reconfigured a plurality of times, in order to enable detecting unit 324 to gather enough data for constructing a curve similar to the curve of FIG. 2.

Optionally, detecting unit 324 is a linear array of detectors, a two-dimensional detector, or a combination of both, and consequently assays a plurality of portions simultaneously, since a plurality of portions, each reflected by a specific area, reach a receiving surface of detecting unit 324. If specimen unit 304 contains a plurality of specimens, and each specimen is in contact with a small area of reflective layer 312, selecting element 326 is moved and/or reconfigured more than once, in order to obtain a complete curve for each specimen.

Optionally, selecting controller 328 is synchronized with detecting unit 324, so that detecting unit 324 makes a measurement only when at least a portion of reflected beam 314 reaches to a receiving surface of detecting unit 324. Optionally, selecting controller 328 instructs detecting unit 324 to make one or more measurements when selecting element 324 is set at specific configurations, according to a predefined and/or dynamic analysis pattern. The synchronization between selecting controller 328 and detecting unit 324 leads to faster assaying of the portions of reflected beam 314.

Figures 5A, 5B:
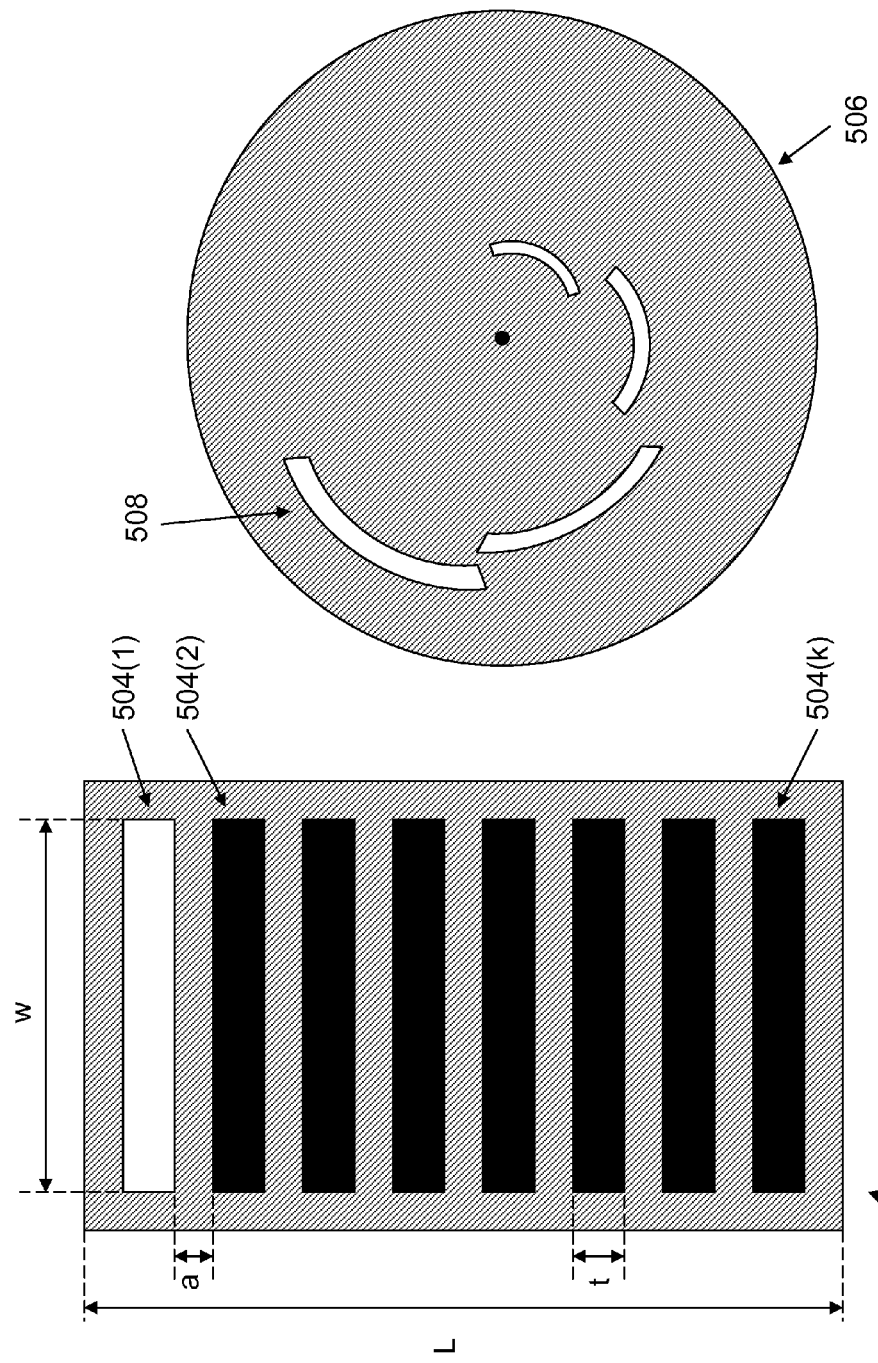
FIGS. 5a and 5b are schematic drawing illustrating different types of arrays of slits, which may be included in a selecting element, according to some embodiments of the present invention.

FIGS. 5a and 5b are schematic drawings illustrating different types of arrays of slits, which may be included in a selecting element, according to some embodiments of the present invention.

According to some embodiments of the present invention, selecting element 326, depicted in FIGS. 3a, 3b, 4a, and 4b, optionally includes a linear array of apertures. FIG. 5a illustrates a linear array 502 having including k apertures, herein referred to as 504(1), 504(2), . . . , 504(k).

Light waves reaching linear array 502 are either blocked by a closed aperture, like 504(2), or transmitted through an open aperture 504(1) toward detecting unit 324. Linear array is characterized by a length "L" an aperture thickness "t", an aperture width "w", and a distance "a" between apertures. The values of the above properties directly affect the magnitude of $d\phi$, which was defined above.

Optionally, linear array 502 is a spatial light modulator. An example of a spatial light modulator is a liquid crystal (LC) linear array controlled by a LC controller. In liquid crystal arrays, slits are usually made of a thin layer of liquid crystal sandwiched between two glass slides, which are, in turn, sandwiched between two polarizers. Optionally, a transparency of each slit is controlled to be selected between an open mode that allows a portion of light directed thereto to pass, and a closed mode that blocks this portion. Optionally, a transparency of each slit is controlled to be selected among a plurality of transparency levels and used, for example, to adjust an intensity of light waves transmitted through the slits. This may be useful for calibration purposes and/or to better ensure working at or near detector saturation levels. According to the LC manufacturing method, each LC slit is connected to a power source that switches between the modes by respective voltages. In such a manner, the linear array 502 allows selected portions to pass toward detecting unit 324 in selected time frames and/or according to predefined and/or dynamic analysis pattern. Optionally, apertures of different sizes can are created by setting one or more adjacent slits into an open mode. Other types of spatial light modulators may be used, for example, diffusing apertured beads, which aperture orientation is controllable by electric fields. Optionally or alternatively, other light modulators known in the art, reflective or transmissive, may be used.

Because of the physical characteristics of LCs, it is possible that the contrast ratio between an LC slit in a blocking mode and an LC slit in an open mode is insufficient. Selecting element 326 optionally includes two or more LC arrays aligned and in series.

LC arrays are characterized by a transition time, which is the average time it takes the slits to change their transparency from a given transparency to a selected transparency. Optionally, selecting element 326 is characterized by a transition time commensurate with the desired speed and/or contrast and/or other system properties.

Because the intensity of reflected light waves varies with the angle of reflection, portions of reflected light 314 which are centered around certain angles of reflection are characterized by higher intensities, which may be above a saturation level of detecting unit 324. According to a common practice in the field, intensity of reflected light 314 is set to be just below a saturation level of detecting unit 324, during a calibration that takes place before the analysis procedure is performed. Optionally, the calibration is performed to maximize the intensity of the light source and therefore increase the signal-to-noise ratio at detecting unit 324. Once the analysis starts, unexpected levels of light (e.g., due to change in source intensity or reflection) may saturate unit 324, and/or damage detecting unit 324. Optionally, such saturation is compensated for by faster image acquisition. However, this may not be possible. According to an embodiment of the present invention, LC controller optionally controls a degree of transparency of LC slits, so that LC slits are set to partially transmit portions centered around selected angles, thereby reducing the intensities of those transmitted portions characterized by intensities higher than the saturation level of detecting unit 324. Optionally, a control of the transparencies is an active control, where the intensity of the emitted light is measured during the analysis process, and if intensity fluctuations are detected (e.g., above a threshold), a signal is sent to the LC controller to change the transparency of the slits accordingly.

In an exemplary embodiment of the invention, the detection is aimed at detecting small changes in a part of the response curve of the sample where the changes in intensity are highest. Optionally, the LC settings are selected to maintain such measurements at a near detector saturation level. Optionally or alternatively, the illumination source is controlled. Generally, however, LC control is more stable, repeatable, fast and/or accurate than light source control.

Since the apertures through which portions pass may be characterized by a small thickness "t", some unwanted diffraction effects may arise. Optionally, the LC controller is configured to affect LC slits, by gradually changing the transparency, and therefore the blocking efficiency, of the LC slits surrounding the aperture transmitting slits. This softens the transition between the areas of the liquid crystal that transmit the light and the areas that block light, and reduces diffraction effects.

It should be noted that there are many types of liquid crystals arrays available today which might be suitable for being included in selecting element 326. An example for such a liquid crystals linear array is a matrix of dot arrays that allows a specific blocking of light.

According to some exemplary embodiments of the present invention, selecting element 326 includes a twisted nematic LC unit, being characterized by 128 slits, a transparency ratio of about 1/100, and a transition time of 1-2 ms. Each slit has a thickness of 0.25 mm, and the thickness "t" of the transmitting apertures on the array is controlled by a choosing a selected number of adjacent slits to be in a transmitting mode.

FIG. 5b depicts a circular array of slits 506 having slits 508. Optionally, each slit 508 is characterized by a constant distance from the center of circular array 506. Selecting element 326 optionally includes circular array of slits 506 and linear array of slits 502. At different moments of the rotation of circular array of slits 506, a different rotating slit 508 is located in front of a different linear slit 504. Therefore, different apertures are created for one or more portions of reflected light 314 to pass through.

Optionally, slits 504 of linear array of slits 502 are thinner than slits 508 of circular array of slits 508. Therefore, when rotating slit 508 moves over slit 504 of linear array 502, the size of the aperture through which one or more portions of reflected light 314 pass is determined by the size of slit 504 of linear array of slits 502.

Optionally, selecting controller 328 controls the torque of circular array of slits 506 and optionally synchronizes the rotational angle of circular array of slits 506 with a sampling frequency defined by detecting unit 324. This enables detecting unit 324 to take a measurement each time a different portion of reflected light 314 passes through selecting element 326. Optionally, selecting controller 328 instructs detecting unit 324 to make one or more measurement when selecting element 326 is set at specific configurations, according to a predefined and/or dynamic analysis pattern.

FIG. 6 is a schematic drawing illustrating a selecting element which includes a linear array of slits and mechanical shutters, according to some embodiments of the present invention.

According to some embodiments of the present invention, selecting element 326 optionally includes a linear array of slits 602 that is characterized by mechanical shutters (606, 608), such that each mechanical shutter (606, 608) is associated with a different slit (604). Mechanical shutters (606, 608) are individually controlled by selecting controller 328, and may be set to be in an open position, like mechanical shutter 606, or in a closed position, like mechanical shutter 608.

In FIG. 6, light waves are reflected by an exemplary area 610 of reflective layer 312, and each light wave is characterized by one of a plurality of angles of reflection. Reflected light 314 reaches linear array 602. A portion 612 of reflected light 312 meets linear array 602 at a slit that is associated with mechanical shutter 606 in an open mode. Portion 612 is therefore transmitted through linear array 602 towards detecting unit 324, and detecting unit 324 measures at least one property of portion 612.

Other portions reflected by area 610 are blocked and do not reach detecting unit 324. For example, portion 614 is blocked by closed mechanical shutter 608, and portion 616 is blocked by the surface of linear array 602.

Optionally, selecting controller 328 reconfigures selecting element 326 by opening a different mechanical shutter at different times, while keeping all other mechanical shutters closed. Therefore, for each configuration, a different portion of light reflected by area 610 is assayed by detecting unit 324.

Optionally, selecting controller 328 synchronizes selecting element 326 with detecting unit 324, so that detecting unit 324 makes one or more measurements only when one or more mechanical shutters are opened. Optionally, selecting controller 328 instructs detecting unit 324 to make one or more measurement when selecting element 326 is set at specific configurations, according to a predefined and/or dynamic analysis pattern.

Optionally, mechanical shutters (606, 608) are moved by one or more of small motors, magnets, solenoids, lead zirconium titanate (PZT) elements, microelectricomechanical system (MEMS) devices, electromagnets, and capacitive elements.

Figures 7A, 7B:
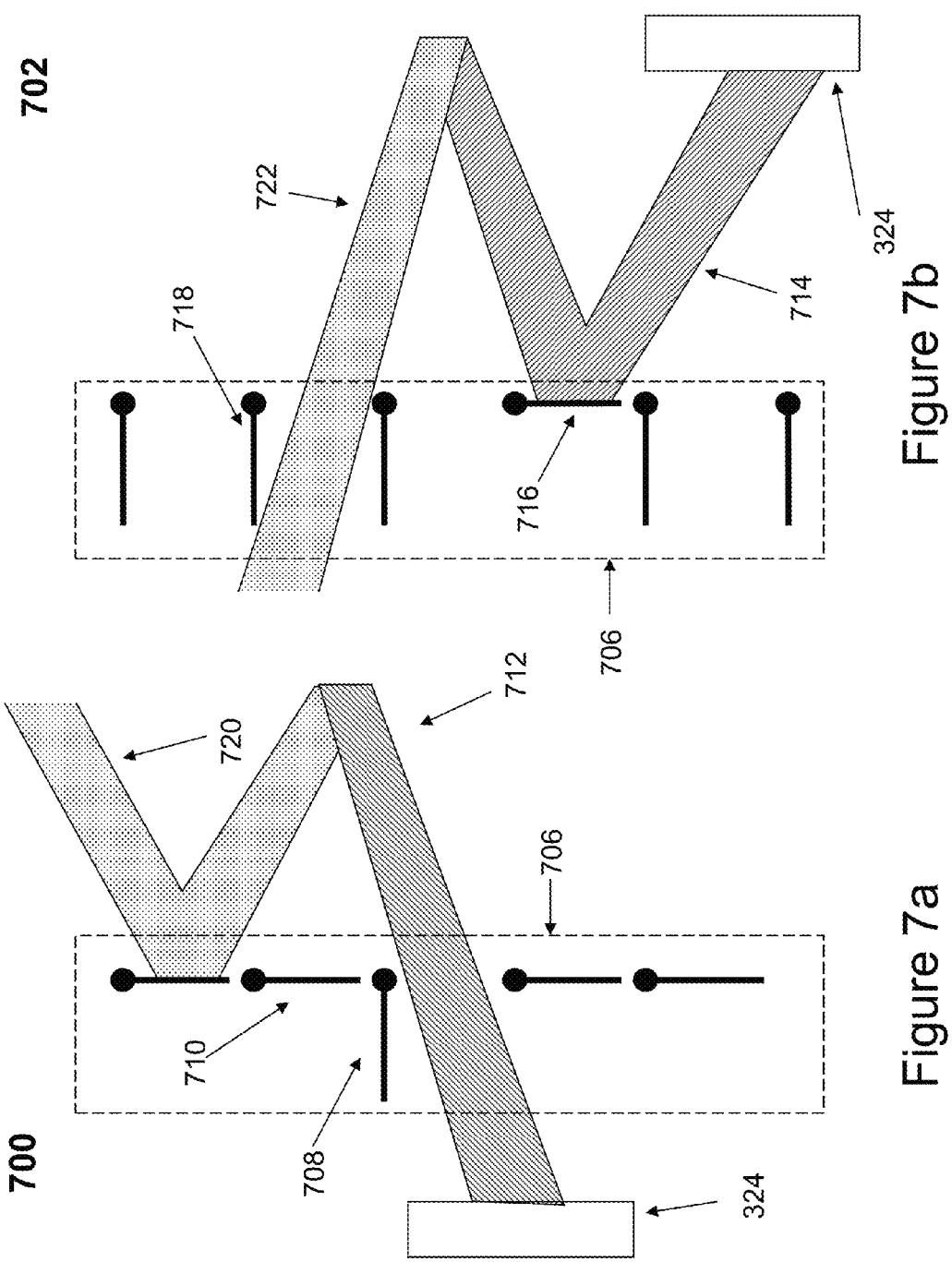
FIGS. 7a and 7b are schematic drawings illustrating two different configurations of a selecting element which includes a linear array of mirrors, according to some embodiments of the present invention.

FIGS. 7a and 7b are schematic drawings illustrating two different configurations of a selecting element which includes a linear array of mirrors, according to some embodiments of the present invention.

According to some embodiments of the present invention, selecting element 326 includes a linear array of mirrors 706. Linear array of mirrors 706 includes a number of mechanically actuated mirrors. Optionally, selecting controller 328 controls each mirror individually, and sets the mirrors to be in open position (708) or a closed position (710). Optionally, the mirrors are moved by one or more of small motors, magnets, solenoids, lead zirconium titanate (PZT) elements, microelectricomechanical system (MEMS) devices, electromagnets, and capacitive elements. Optionally, the mirrors are provided as a digital light processing (DLP) device (e.g., an array of microscopic mirrors formed on a substrate and with electrical reflection angle control).

In FIG. 7a, embodiment 700 is depicted, according to which linear array of mirrors 706 and detecting unit 324 are positioned to allow portions of reflected light 314 to pass through linear array of mirrors 706 toward detecting unit 324. Portion 712 passes through linear array of mirrors 706 toward detecting unit 324. All other portions reflected by the same area of reflective layer 312 as portion 712—such as portion 720—are reflected by linear array of mirrors 706, for example as shown at 710.

Reference is now also made to FIG. 7b, which is a schematic illustration of another configuration of a selecting element that includes a linear array of mirrors 706, according to some embodiments of the present invention. FIG. 7b depicts detecting unit 324 and a linear array of mirrors 706 which are positioned relative to each other in a manner that the portions of reflected light 314 may be reflected by linear array of mirrors 706 toward detecting unit 324. A portion 714 of the reflected light 314 is reflected by linear array of mirrors 706 toward detecting unit 324. All other portions reflected by the same area of reflective layer 312 as portion 714—such as portion 722—pass through the open mirrors of linear array of mirrors 706, for example as shown at 718.

In both embodiments 700 and 702, linear array of mirrors 706 is reconfigured and/or moved, optionally by selecting controller 328, by changing the orientation and/or positioning on the mirrors, so that different portions reflected by the same area of reflective layer 312 as portion 714 reach detecting unit 324 at different times, and are therefore individually assayed by detecting unit 324.

Optionally, array of mirrors 706 provides efficient selecting, as non-selected portions of light are reflected by mirrors away from detecting unit 324 or otherwise do not continue towards the detector. Optionally, array of mirrors 706 is characterized by a short switching time between configurations, and is therefore able to sequentially select a greater number of light portions in a short amount of time.

Optionally, selecting controller 328 synchronizes linear array of mirrors 706 with detecting unit 324, so that detecting unit 324 makes one or more measurements only when linear array of mirrors 706 directs portions of light to detecting unit 324, for example by mirror 716. Optionally, selecting controller 328 instructs detecting unit 324 to make one or more measurement when linear array of mirrors 706 is set at specific configurations, according to a predefined and/or dynamic analysis pattern.

Figure 8:
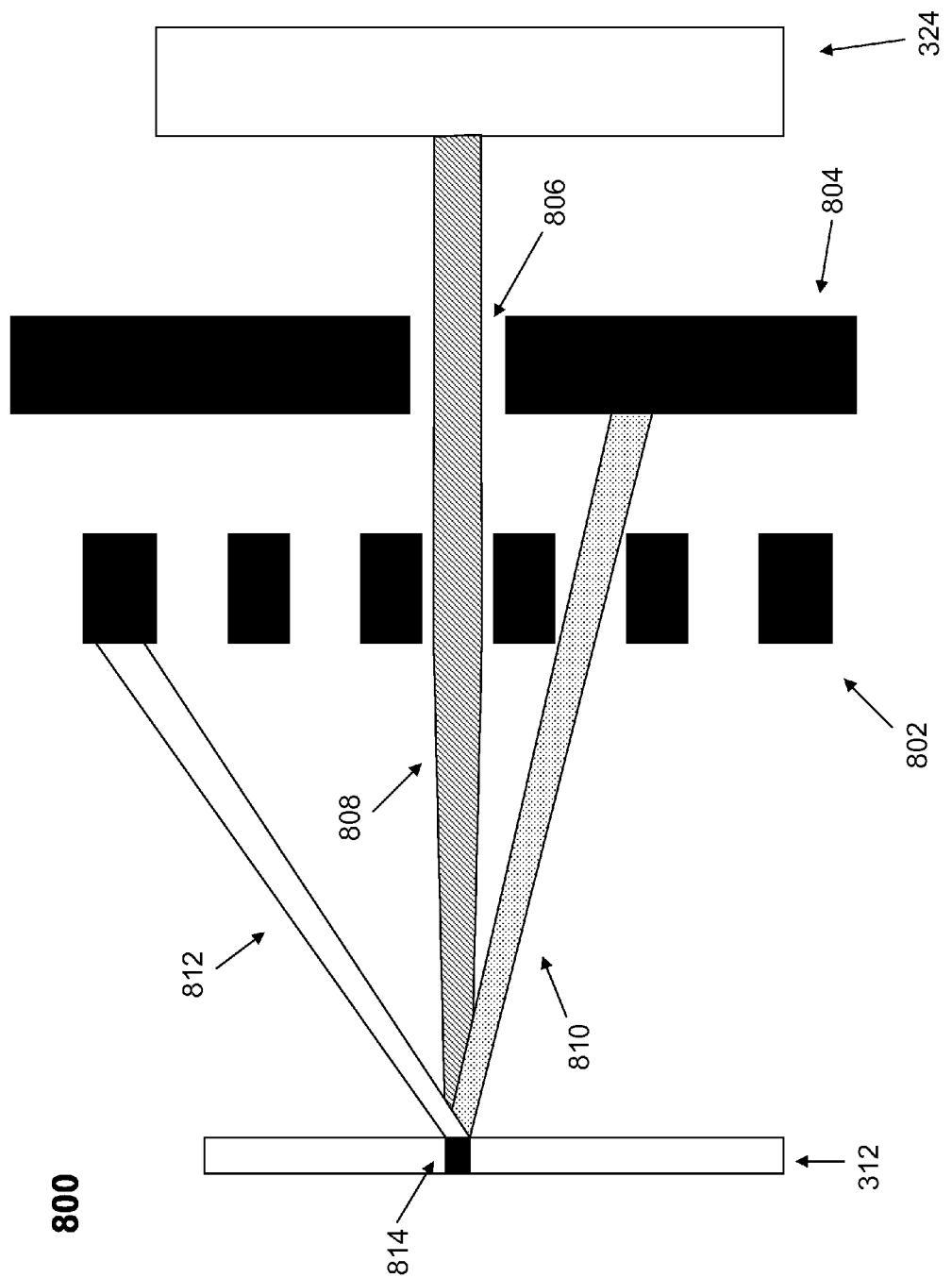
FIG. 8 is a schematic drawing illustrating a cross section of a selecting unit which includes of a linear array of slits and a mask having only one slit, according to some embodiments of the present invention

FIG. 8 is a schematic drawing illustrating a cross section of a selecting unit which includes a linear array of slits and a mask having a single slit, according to some embodiments of the present invention.

According to some embodiments of the present invention, selecting element 326 includes element 800, which is made of a linear array of slits 802, and a mask 804 with one slit 806.

In FIG. 8, light is reflected by an exemplary area 814 of reflective layer 312 encounters element 800. Portions of the reflected light, which encounter the slits on linear array of slits 802, pass through linear array of slits 802. Out of the above portions, only one portion 808 is transmitted toward detecting unit 324 through slit 806 of mask 804, since slit 806 coincides with one of the slits of linear array of slits 802. Other portions—like portion 810, for example—are blocked by mask 804. Some portions—like portion 812, for example—are blocked by the surface of linear array of slits 802.

Optionally, selecting controller 328 controls the relative movement between linear array of slits 802 and mask 804. Selecting controller 328 reconfigures element 800, by setting slit 806 in front of different slits of linear array of slits 802 at different times, thus ensuring other portions reflected by area 814 reach detecting unit 324, one portion for each configuration. Optionally, linear array of slits 802 is fixed and selecting controller 328 controls the movement of mask 804. Optionally, slit 806 of mask 804 is larger than the slits of linear array of slits 802, so that the size of aperture through which the portions of reflected light 314 pass is determined by the size of the slits of linear array of slits 802.

Optionally, selecting controller 328 synchronizes element 800 with detecting unit 324, so that detecting unit 324 makes one or more measurements only when slit 806 of mask 804 and one of the slits of linear array of slits 802 create an aperture through which one or more portions of reflected light 314 pass. Optionally, selecting controller 328 instructs detecting unit 324 to make one or more measurement when selecting element 326 is set at specific configurations, according to a predefined and/or dynamic analysis pattern.

Figure 9:
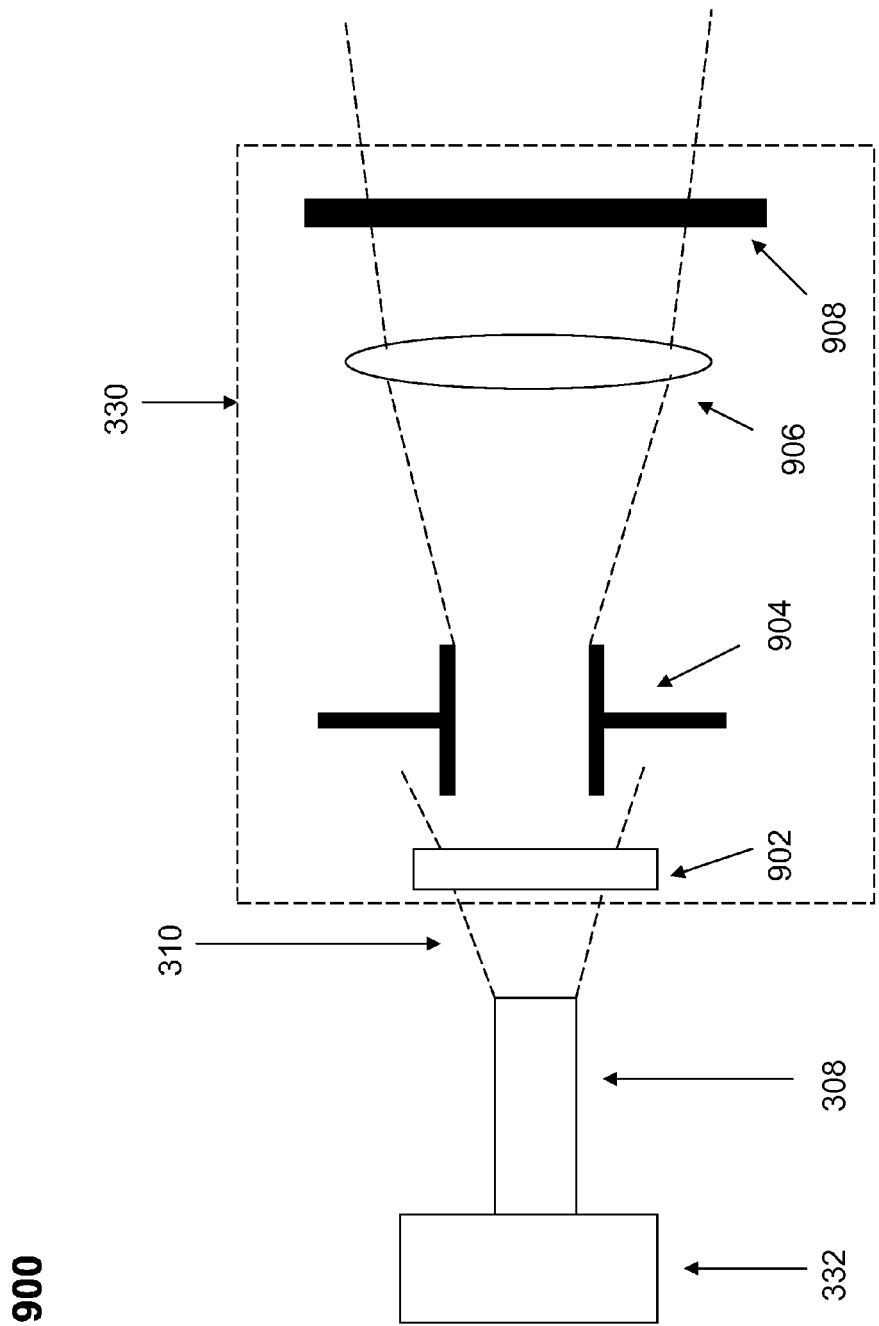
FIG. 9 is a schematic drawing illustrating in detail a lighting subsystem belonging to the system depicted in FIGS. 3a and 3b, according to some embodiments of the present invention.

FIG. 9 is a schematic drawing illustrating in detail an illumination subsystem belonging to the system depicted in FIG. 3a, according to some embodiments of the present invention.

Illumination subsystem 900 is an exemplary subsystem, which may be substituted to illumination subsystem 302 shown in FIG. 3a. Subsystem 900 includes light source 308 and an optical control sub-apparatus 330 of an illumination control apparatus, as defined above. Light source 308 emits illuminating light 310. Optical control sub-apparatus 330 is configured before a start of an analysis procedure, in order to set at least one property of illuminating light 310.

Optionally, subsystem 900 further includes a temperature control sub-apparatus 332, to control the temperature of light source 308. Optionally, temperature control apparatus 332 is used to set a temperature of light source 308 before an analysis procedure, and keep the temperature constant for the duration of the analysis procedure, as explained above.

Optionally, optical control apparatus 330 includes one or more diffusers 902, for improving the angle distribution of light waves within illuminating light 310. Optionally, optical control apparatus 330 includes one or more angle stops 904, for controlling the range of angles of incidence of illuminating light 310. Optionally, optical control apparatus 330 includes one or more collimators 906, to reduce the range of angles of incidence of illuminating light 310. Optionally, optical control apparatus 330 includes one or more polarizers 908, for polarizing illuminating light 310, in order to block the s-polarized light, which does not interact with the optical analysis system.

In the embodiment shown in FIG. 9, light source 308 emits illuminating light 310. Illuminating light 310 passes through diffuser 902, angle stop 904, collimator 906, and polarizer 908, in sequence. It should be noted that it is possible to control properties of illuminating light 310 through one, some, or all of the above elements, and that other configurations may be used, in which the above elements are placed in a different order.

Optionally, diffuser 902 includes one or more or a combination of glass diffusers, Teflon diffusers, holographic diffusers, opal glass diffusers, and greyed glass diffusers. Optionally, angle stop 904 includes one or more of irises and flips. Optionally, collimator 906 includes one or more of positive lenses, arrays of lenses curved reflectors, Fresnel zones lenses, and diffracting elements. Optionally, polarizer 908 includes one or more absorptive polarizers and beam-splitting polarizers.

Figure 10:
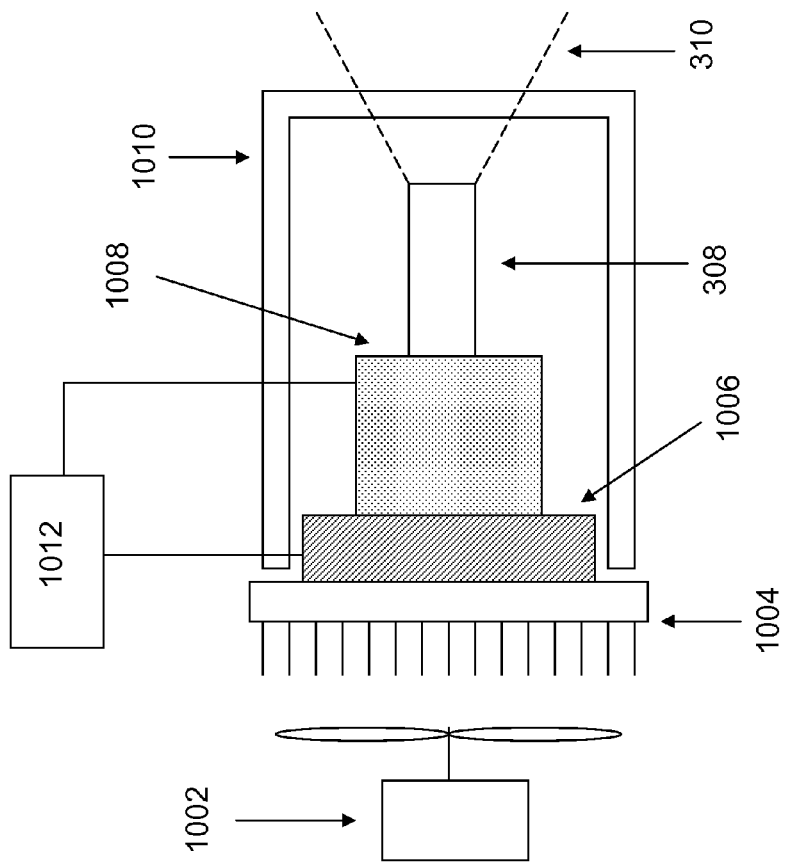
FIG. 10 is a schematic drawing illustrating in detail a temperature control apparatus, according to some embodiments of the present invention.

FIG. 10 is a schematic drawing illustrating in detail a temperature control sub-apparatus 332 of illumination control apparatus described in FIGS. 3a and 9, according to some embodiments of the present invention.

Optionally, temperature control apparatus 332 includes one or more of a fan 1002, a heat sink 1004, a thermoelectric unit 1006, an heat conducting block 1008, and an isolation case 1010. Fan 1002 and heat sink 1004 are configured to decrease the temperature of light source 308. Thermoelectric unit 1006 is configured to be controlled by thermoelectric control unit 1012 in order to increase or decrease the temperature of light source 308. Optionally, thermoelectric unit includes one or more of a Peltier thermoelectric device (for heating and/or cooling), or one or more resistors or other heating element, with cooling being continuously applied by other means. Heat conducting block 1008 is optionally made of Aluminum. Heat conducting block 1008 in contact with light source 308 and is configured for conducting heat to light source 308 from thermoelectric unit 1006, or from light source 308 to thermoelectric unit 1006 light source 308. Isolation case 1010 is configured to keep the temperature of light source 308 constant, by isolating light source 308 from the surroundings.

Optionally, thermoelectric control unit 1012 is connected to heat conducting block 1008 (and/or to a temperature sensor thereon), in order to measure a temperature of heat conducting block 1008 at a location near light source 308. According to a measured value of the temperature, thermoelectric control unit controls thermoelectric 1006 to increase or decrease a temperature thereof, in order to keep the temperature of light source 308 constant. Optionally or alternatively, the light source temperature is estimates based on an intensity and/or frequency of light detected from the source via a separate detector (not shown).

Figure 11:
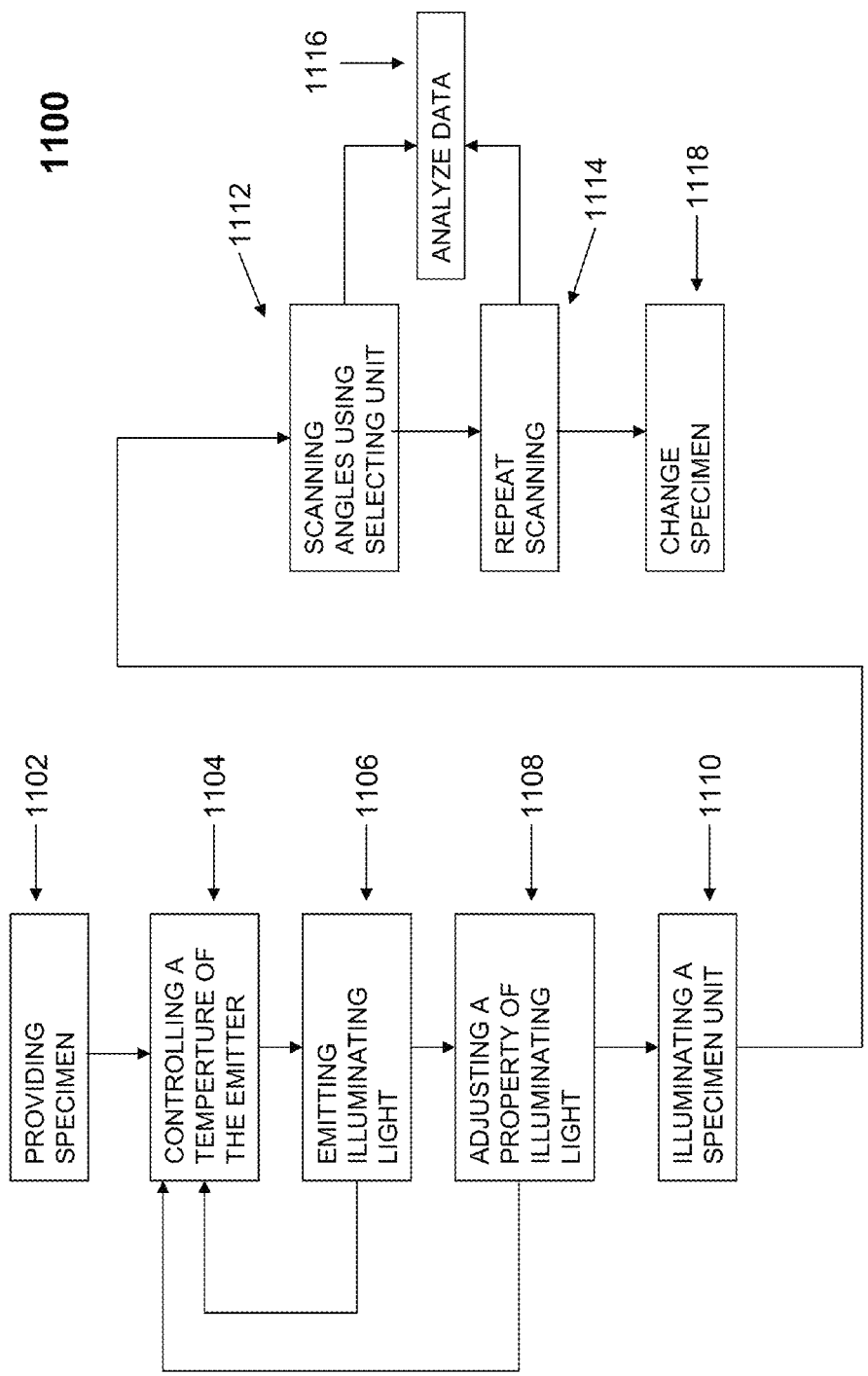
FIG. 11 is a flowchart illustrating a method for analyzing at least one property of at least one reaction of a specimen in an optical resonance analysis system.

FIG. 11 is a flowchart illustrating a method for analyzing at least one property of at least one specimen in an optical resonance analysis system, according to some embodiments of the present invention.

Optionally, the optical resonance analysis system is one of a SPR analysis system, a TIR analysis system, Brewster's angle analysis system, and an ellipsometry analysis system. At 1102, a one or more specimens are provided and placed at a specimen unit, optionally according to the method featured in U.S. patent application Ser. No. 10/578,860 mentioned above. Optionally, the system is calibrated according to the specimen being detected, for example, with parameters for an expected SPR curve. Optionally or alternatively, the system is calibrated to ensure maximum sensitivity, for example, ensuring detector operation at near saturation.

At 1104, a temperature of a light source is set and controlled.

At 1106, the light source emits light.

At 1108, at least one property of the emitted light is controlled, optionally by an illumination control apparatus, as described above. Optionally, the property is one of intensity, wavelength, polarization, angular distribution, and angular range.

At 1110, the specimen unit is illuminated by the emitted light at a plurality of locations, each location being illuminated at a range of incidence angle $\Delta\phi_i$, as defined above. Optionally the specimen unit is illuminated by light characterized by a range of wavelengths.

At 1112, a set one or more portions of light reflected by or refracted through the specimen unit is selected according to a span of angles of reflection, a span of angles of refraction, and/or a span of wavelengths, and scanned by a detecting unit, as described above. The selecting unit is reconfigured to choose different sets of one or more portions, and the scanning is repeated.

At 1114, the scanning may be repeated, for example, to provide a running time average of the measurements. The data from all scannings is analyzed at 1116. 1112 and 1114 may be repeated multiple times.

Once the scanning of the one or more specimen is complete, the specimen are changed at 1118, and the process may be repeated. In some cases, the specimen changes in a continuous manner (e.g., flow through).

It is expected that during the life of a patent maturing from this application many relevant optical resonance analysis systems will be developed and the scope of the term "optical resonance analysis system" is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the present invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Two experiments have been performed with a SPR analysis system, shown in FIG. 3*b*. The system including a light source 308 including a plurality of LEDs emitting monochromatic light with a wavelength of 690 nm, 20 nm FWHM, covered by a diffuser 330*a*; a collimation lens 330*b* from Edmund Optics having a focal length of 18 mm, set 18 mm the diffuser of the light source; a frontal lens 346*a* from Newport Corporation having a focal length of 63.5 mm, set 63.5 mm after reflective layer 312 and 63.5 mm before a selecting element; a selecting element characterized by a single manually movable slit; and a rear lens 348*a* from Newport Corporation having a focal length of 100 mm, set after the selecting element and 100 mm before a detector.

Experiment 1

The purpose of the first experiment was to find an advantageous size for a slit on the selecting element.

Figure 12:
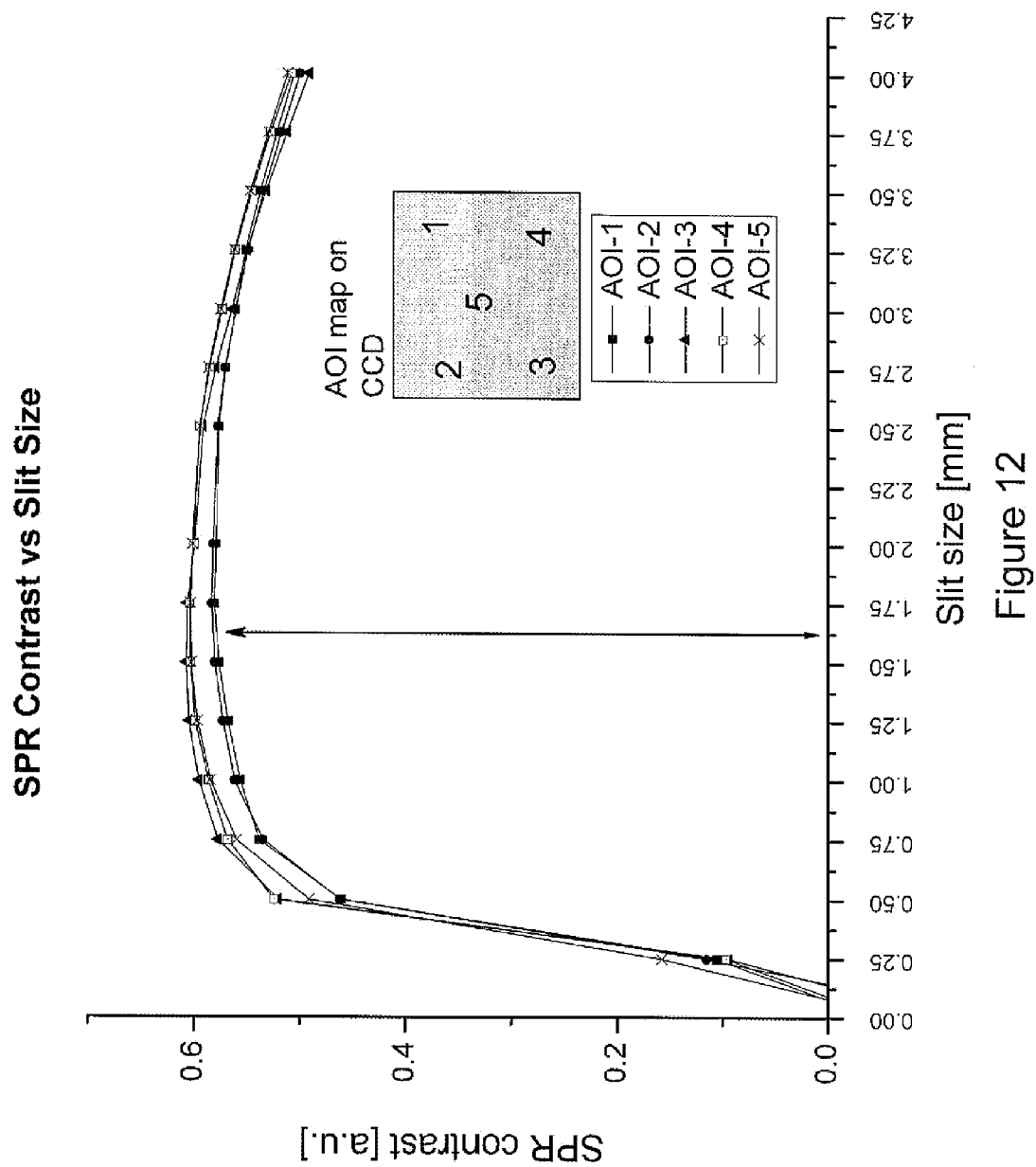
FIG. 12 is a graph of SPR contrast as a function of slit size, according to an experiment performed with an embodiment of the present invention.

A light beam was emitted to illuminate the reflective layer of the SPR analysis system, and the intensity of the reflected beam was measured, after the reflected beam was filtered by a selecting unit having a slit of variable size, before falling onto a two dimensional CCD detector. The size of the slit was plotted against the contrast between the channel area and the surrounding silicon rubber area for each slit width at five different locations on the reflective layer surface, the locations being referred to as AOI-1 to AOI-5. The contrast was calculated through equation 1:

$$\text{contrast} = \frac{I_{RTV} - I_{SPR}}{I_{RTV} + I_{SPR}} \quad [\text{EQ. 1}]$$

where $I_{RTV}$ and $I_{SPR}$ are the measured intensities at the silicon rubber area and the SPR area, respectively. A high value of contrast indicated a better resolution, and therefore better sensitivity of the SPR system. The results of the first experiment are shown in FIG. 12. It has been found that an advantageous slit size is between 1.5 mm and 1.75 mm. The sensitivity of the system is expected to be better than 0.1 RU, for example, 0.01 RU or 0.05 RU, each RU being a $10^{-6}$ change in the refractive index.

Experiment 2

The purpose of the second experiment was to test the dynamic range of an embodiment of the present invention featuring an SPR analysis system. The dynamic range of an SPR systems defines the magnitude of the shifts in "intensity vs. angle of reflection" curves, that the SPR system can measure. The higher the dynamic range is, the larger the measurable shift is.

The dynamic range was tested with a setup described above, further featuring a movable slit of width 1.5 mm, and a detector including a CCD sensor, set to take an intensity measurement at a single area of interest. The system was tested with specimens of glucose solutions having concentration of 0% (DDW), 140 mg/ml, 280 mg/ml, 420 mg/ml, and 560 mg/ml, each having a known refractive index. The difference in refractive index between the first and last specimens corresponds to a dynamic range of about 80K RU.

The 0% glucose solution was placed in the flow channel the specimen unit and was tested first. The slit was moved along a cross section of the selecting unit, so that at each position of the slit, the detecting unit measured the intensity of a portion of the reflected light, characterized by a different angle of reflection. After the measurements were completed, intensity was plotted as a function of slit position, which in this case is the same as intensity as a function of angle of reflection. The obtained curve was normalized with frames taken with a dry flow channel.

Figure 13:
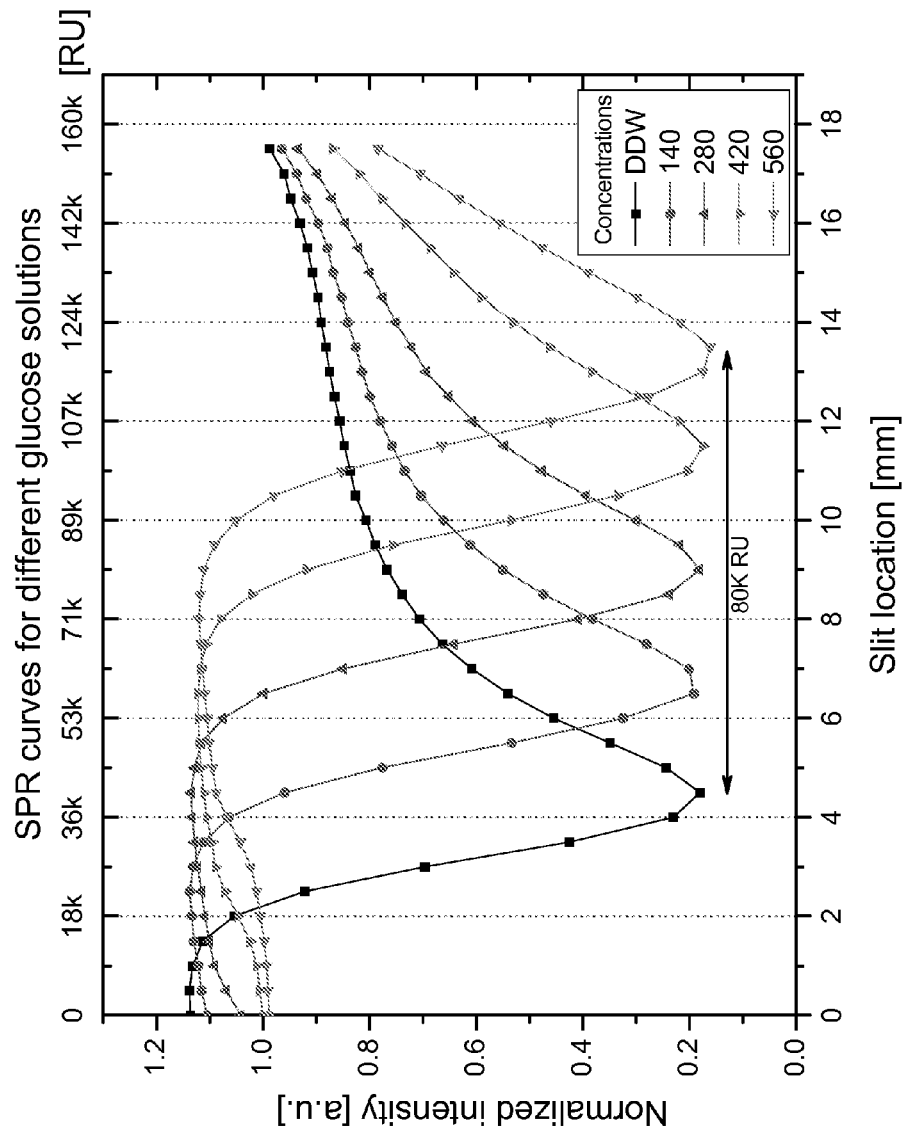
FIG. 13 is a graph of intensity as a function of slit position, according to an experiment performed with an embodiment of the present invention.

The experiment was repeated once for each glucose solution, and the plotted curves are shown in FIG. 13. It is known that the relation of intensity and angle of reflection is proportional to the relation of intensity and refractive index change. Therefore, intensity as a function of angle of reflection and intensity as a function of refractive index difference may be represented by the same curve, as it is done in FIG. 13, in order to determine the dynamic range of the system, measured in RU.

In FIG. 13, it can be seen that the full theoretical dynamic range covers almost 160K RU (measured from left to right, full scale). A practical dynamic range includes the middle portion of the full theoretical dynamic range, as light which is detected at large angles (on the left and right sides of the graph) is characterized by a quickly falling intensity, which corresponds to a lower sensitivity of the SPR system. According to an exemplary embodiment of the present invention, the practical dynamic range is of about 80K RU.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An optical resonance analysis system, comprising:
at least one light source which emits an illumination;
a specimen unit which holds at least one specimen and configured for facilitating interaction between said specimen and said illumination, said illumination providing a plurality of angles of incidence simultaneously, said interacting including one or both of reflecting part of said illumination, and refracting part of said illumination;
a detection unit configured to detect at least part of said illumination after said interaction; and
a selecting unit which selects only a portion of said interacted light for detection by the detection unit, said portion representing interactions with light at less than a full range of said plurality of angles of incidence and wherein said selecting unit is reconfigured for selecting at least a different one of said portions, at different times.

2. The system of claim 1, wherein said selecting unit selects at least one portion of said reflected illumination.

3. The system of claim 1, wherein said illumination illuminates at least one location of said specimen unit at a range of continuous angles of incidence.

4. The system of claim 1, wherein said light source is maintained in a stable illumination state for at least 1 second.

5. The system of claim 1, wherein said light source comprises only a single light source.

6. The system of claim 1, wherein said selecting unit selects said portion in chosen time frames, according to at least one selected analysis pattern.

7. The system of claim 1, wherein said selecting unit and said detecting unit are synchronized, said detecting unit taking measurements only when portions selected by said selecting unit reach said detecting unit.

8. The system of claim 1, wherein said selecting unit is positioned about at a Fourier plane of lens used to image said reflecting surface onto said detector.

9. The system of claim 1, wherein said selecting unit comprises:
a plurality of shutters selectively controllable to selectively transmit said portion to said detecting unit.

10. The system of claim 1, wherein said selecting unit comprises a plurality of mirrors, configured to selectively convey said portion to said detecting unit.

11. The system of claim 1, wherein the optical resonance analysis system comprises one or more of a surface plasmon resonance (SPR) analysis system, a total internal reflectance (TIR) analysis system, an ellipsometric analysis system, and a Brewster angle analysis system, and said detecting unit is configured for measuring one or both of a light wave polarization and a light wave intensity.

12. A screening system including an optical resonance analysis system according to claim 1, comprising:
a plurality of reservoirs each holding a specimen; and
a specimen delivery apparatus connected to the reservoirs, configured for delivering specimens from the reservoirs to the specimen unit.

13. The system of claim 1, wherein said specimen unit is divided into a plurality of analysis areas, each analysis area potentially containing a different specimen.

14. The system of claim 1, wherein said detecting unit further captures a spatially continuous image of said specimen unit as illuminated by said light source.

15. The system of claim 1, wherein said selecting unit selects said portion, to select a substantially single angle of incidence of said plurality of angles.

16. The system of claim 13, wherein a plurality of specimens are analyzed simultaneously.

17. The system of claim 14, wherein said continuous image is a two dimensional image.

18. The system of claim 17, comprising a processing unit associated with said detecting unit and which selects a plurality of non-contiguous sections of said two dimensional image for further processing.

19. The system of claim 15, wherein said selecting unit comprises an array of liquid crystal elements, wherein a degree of transparency of each of said liquid crystal elements is controlled, for transmitting said portions to said detecting unit or for blocking said portions or for decreasing an intensity of said portions.

20. The system of claim 15, wherein said selecting unit comprises:
 a first mask having at least one aperture; and
 a second mask having at least one aperture linear array of slits; and
 a mask mover configured to move one or both masks such that said selecting depends on a an alignment of said masks.

21. The system of claim 19, wherein said transparency of each said liquid crystal element is controlled to provide a gradual change between an area which transmits said portions and adjacent areas which block said portions, in a manner which reduces at least some diffractive effects.

22. The system of claim 20, wherein said first mask comprises a circular array of slits.

23. The system of claim 20, wherein said second mask comprises a linear array of slits.

24. A method for detecting at least one property of at least one specimen in an optical resonance analysis system, comprising:
 illuminating a specimen with illumination light at a plurality of angles of incidence simultaneously, to provide modified light;
 virtually selecting only a portion of said illumination light by selecting only a portion of said modified light, said selected portion of modified light corresponding to illumination light at only a subset of said angles of incidence; and
 detecting a signal on said selected modified light.

25. The method of claim 24, wherein said selecting comprises:
 selecting a plurality of different sets, each set comprising at least one portion, at different times.

26. The method of claim 24, wherein said detecting comprises one or more of:
 measuring an intensity of said portion; and
 measuring a polarization of said portion.

27. The method of claim 24, wherein the optical resonance analysis system is a surface plasmon resonance (SPR) analysis.

* * * * *